US009171201B2

(12) United States Patent
Lake, II et al.

(10) Patent No.: US 9,171,201 B2
(45) Date of Patent: Oct. 27, 2015

(54) PORTABLE COMPUTING DEVICE AND ANALYSES OF PERSONAL DATA CAPTURED THEREFROM

(71) Applicant: ATLAS WEARABLES, INC., Austin, TX (US)

(72) Inventors: Thomas Lee Lake, II, Portage, MI (US); Michael Kasparian, Andover, MA (US); Peter Li, Sunnyvale, CA (US)

(73) Assignee: ATLAS WEARABLES, INC., Austin, TX (US)

( * ) Notice: Subject to any disclaimer, the term of this patent is extended or adjusted under 35 U.S.C. 154(b) by 0 days.

(21) Appl. No.: 14/447,562

(22) Filed: Jul. 30, 2014

(65) Prior Publication Data

US 2015/0005911 A1    Jan. 1, 2015

Related U.S. Application Data

(60) Provisional application No. 61/828,680, filed on May 30, 2013.

(51) Int. Cl.
*A63B 69/00* (2006.01)
*G06K 9/00* (2006.01)
(Continued)

(52) U.S. Cl.
CPC ............ *G06K 9/00342* (2013.01); *A63B 71/06* (2013.01); *G06Q 50/22* (2013.01); *A63B 2220/34* (2013.01); *A63B 2220/40* (2013.01);
(Continued)

(58) Field of Classification Search
CPC .... G09B 19/0038; G06F 19/3481; G06T 7/20
USPC ........................................................ 434/247
See application file for complete search history.

(56) References Cited

U.S. PATENT DOCUMENTS 5,446,775 A    8/1995   Wright et al.
5,891,042 A    4/1999   Shamm et al.
(Continued)

FOREIGN PATENT DOCUMENTS

WO    WO-2013-098791    7/2013

OTHER PUBLICATIONS

PCT/US2014/048972 International Search Report and Written Opinion dated Nov. 13, 2014.
(Continued)

*Primary Examiner* — Xuan Thai
*Assistant Examiner* — Michael Grant
(74) *Attorney, Agent, or Firm* — Wilson Sonsini Goodrich & Rosati

(57) ABSTRACT

A personal computing device comprising: a processor, an onboard memory, an accelerometer, a gyroscope, and a display; a computer program to create an exercise analysis application comprising: a software module configured to receive data from the accelerometer and the gyroscope that are associated with the bodily motion of a user in three dimensions; a software module configured to place the device in a learning mode, the learning mode comprising recording the data of the user performing a defined exercise to generate a statistical model for the exercise; a software module configured to place the device in a normal mode, the normal mode comprising applying a probabilistic analysis to the bodily motion data to identify an exercise event, classify the exercise by comparison to a recorded model; and a software module configured to apply an analysis to the bodily motion data to score the user's exercise form.

30 Claims, 11 Drawing Sheets

(51) Int. Cl.
*A63B 71/06* (2006.01)
*G06Q 50/22* (2012.01)
*G06T 7/20* (2006.01)
*G06F 19/00* (2011.01)
*G09B 19/00* (2006.01)

(52) U.S. Cl.
CPC ......... *A63B 2230/06* (2013.01); *A63B 2230/40* (2013.01); *A63B 2230/50* (2013.01); *A63B 2230/65* (2013.01); *G06F 19/3481* (2013.01); *G06T 7/20* (2013.01); *G09B 19/0038* (2013.01)

(56) References Cited

U.S. PATENT DOCUMENTS

| | | | |
|---|---|---|---|
| 6,358,188 | B1 | 3/2002 | Ben-Yehuda et al. |
| 7,454,002 | B1 | 11/2008 | Gardner et al. |
| D637,094 | S | 5/2011 | Cobbett et al. |
| D637,918 | S | 5/2011 | Cobbett et al. |
| 8,371,989 | B2 | 2/2013 | Kim et al. |
| 8,725,842 | B1 | 5/2014 | Al-Nasser |
| D725,511 | S | 3/2015 | Read et al. |
| D725,512 | S | 3/2015 | Read et al. |
| 2003/0109258 | A1 | 6/2003 | Mantyjarvi et al. |
| 2005/0210419 | A1 | 9/2005 | Kela et al. |
| 2007/0032981 | A1 | 2/2007 | Merkel et al. |
| 2007/0135225 | A1 | 6/2007 | Nieminen et al. |
| 2007/0260482 | A1 | 11/2007 | Nurmela et al. |
| 2007/0270214 | A1 | 11/2007 | Bentley |
| 2008/0090703 | A1* | 4/2008 | Rosenberg .................. 482/8 |
| 2009/0221403 | A1 | 9/2009 | Chan et al. |
| 2009/0312152 | A1 | 12/2009 | Kord |
| 2010/0063813 | A1 | 3/2010 | Richter et al. |
| 2010/0204952 | A1 | 8/2010 | Irlam et al. |
| 2011/0306469 | A1 | 12/2011 | Klabunde et al. |
| 2012/0046907 | A1* | 2/2012 | Scott ........................... 702/151 |
| 2012/0129138 | A1* | 5/2012 | Redmann .................... 434/247 |
| 2012/0194976 | A1 | 8/2012 | Golko et al. |
| 2012/0272194 | A1 | 10/2012 | Yang et al. |
| 2012/0323496 | A1 | 12/2012 | Burroughs et al. |
| 2012/0323521 | A1 | 12/2012 | De Foras et al. |
| 2013/0150121 | A1* | 6/2013 | Jeffery et al. ............ 455/556.1 |
| 2013/0190908 | A1 | 7/2013 | Ellis et al. |
| 2013/0338802 | A1* | 12/2013 | Winsper et al. ................. 700/92 |
| 2014/0074265 | A1* | 3/2014 | Arginsky et al. ............... 700/91 |
| 2014/0081156 | A1* | 3/2014 | Ohsawa ......................... 600/483 |
| 2014/0163704 | A1* | 6/2014 | DePietro et al. ................. 700/91 |
| 2014/0270375 | A1* | 9/2014 | Canavan et al. .............. 382/103 |
| 2014/0278229 | A1* | 9/2014 | Hong et al. ................... 702/160 |
| 2014/0330408 | A1* | 11/2014 | Rolley ............................. 700/91 |
| 2015/0072326 | A1* | 3/2015 | Mauri et al. .................. 434/247 |

OTHER PUBLICATIONS

U.S. Appl. No. 29/497,899, filed Jul. 29, 2014, Read et al.
U.S. Appl. No. 29/497,903, filed Jul. 29, 2014, Read et al.
Wilson et al. Gesture recognition using the Xwand. Carnegie Mellon University. Robotics Institute. 2004. 13 pgs.
Proceedings of Gesture-based Interaction Design: Communication and Cognition. 2014 CHI Workshop Toronot, Canada. Apr. 26, 2014. 85 pgs. Available at http://hci.uncc.edu/~mmaher9/CHI-gestureinteraction/papers/GestureBasedInteraction_CHIWorkshop_Proceedings.pdf.
Mattmann et al. Recognizing Upper Body Postures Using Textile Strain Sensors. IEEE Wearable Computers, 2007 11th IEEE International Symposium Boston, MA. Oct. 11-13, 2007. pp. 29-36. Available at http://ieeexplore.ieee.org/xpl/login.jsp?tp=&arnumber=4373773&url=http%3A%2F%2Fieeexplore.ieee.org%2Fxpls%2Fabs_all.jsp%3Farnumber%3D4373773.
https://amiigo.com/ (Accessed Aug. 2014).
www.amiigo.com (Accessed Aug. 2014).
http://rithmio.com/ (Accessed Aug. 2014).
www.thalmic.com (Accessed Aug. 2014).
https://www.liveathos.com/ (Accessed Aug. 2014).
http://www.gettrainr.io/ (Accessed Aug. 2014).
http://www.motionx.com/home/technology (Accessed Aug. 2014).
https://www.indiegogo.com/projects/leo-fitness-intelligence#home (Accessed Aug. 2014).
https://www.kickstarter.com/projects/freewavz/freewavz-smart-earphones-with-built-in-fitness-mon (Accessed Aug. 2014).
http://blog.adidas-group.com/2014/07/in-a-bid-to-win-the-world-cup-dfb-team-makes-the-most-of-cutting-edge-technology/ (Accessed Aug. 2014).
U.S. Appl. No. 29/497,903 Office Action dated Jan. 2, 2015.

* cited by examiner

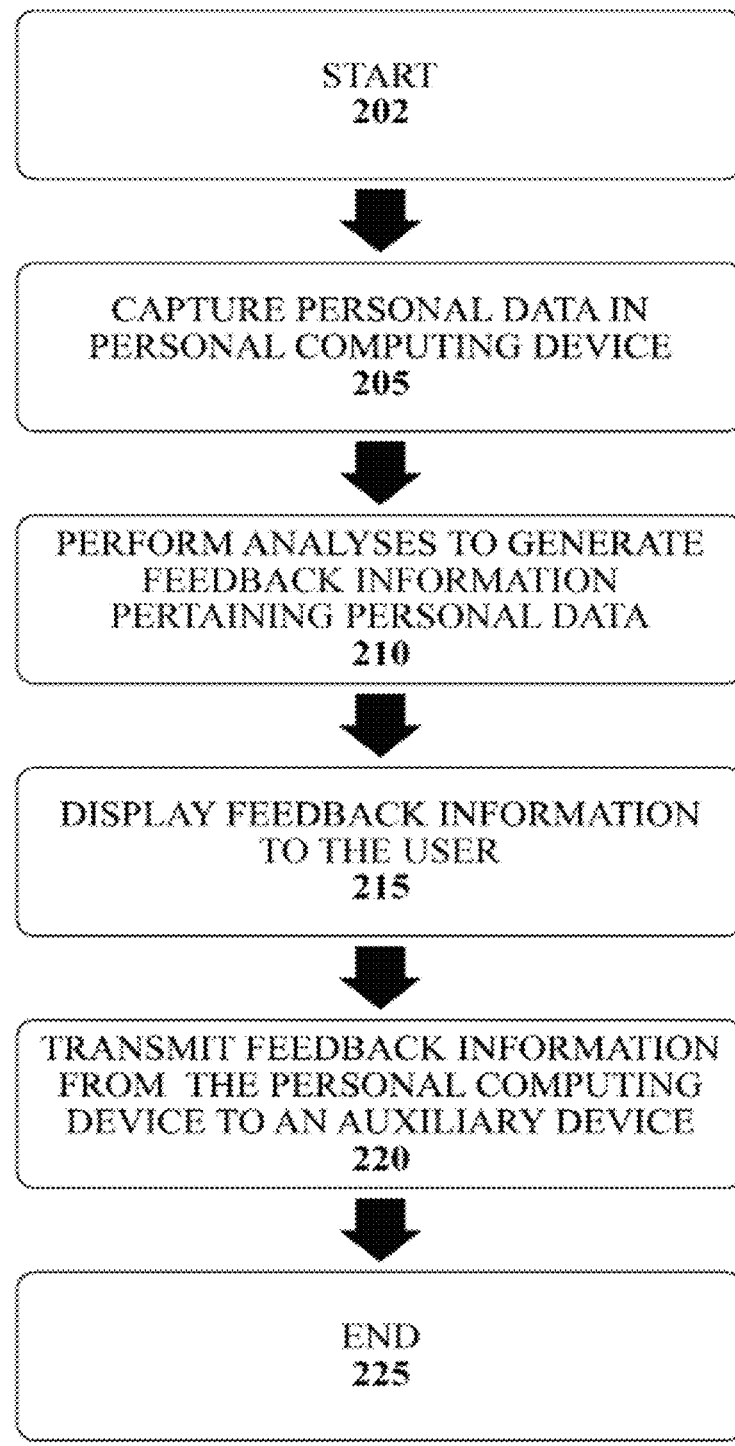

FIG. 6
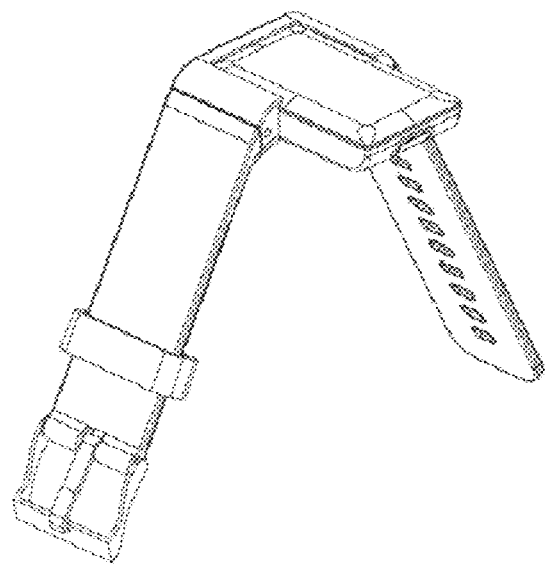
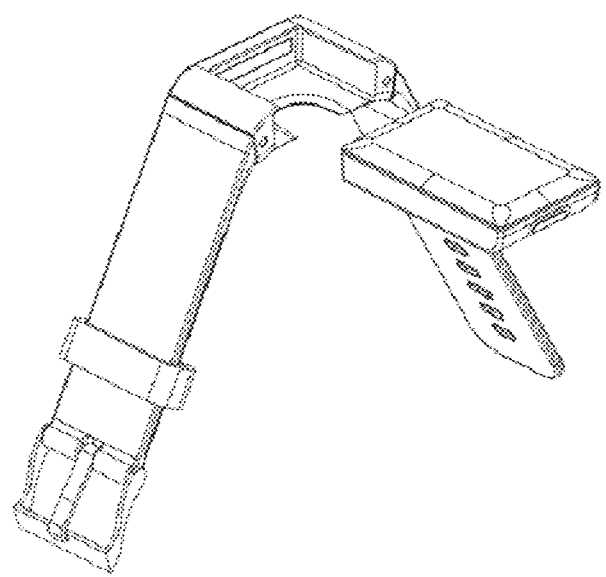

PORTABLE COMPUTING DEVICE AND ANALYSES OF PERSONAL DATA CAPTURED THEREFROM

CROSS-REFERENCE TO RELATED APPLICATIONS

The present application is a non-provisional of, and claims the benefit of, U.S. Provisional Application No. 61/828,680 filed on May 30, 2013, the entire contents of which are incorporated herein by reference.

BACKGROUND OF THE INVENTION

Physical fitness is beneficial to a person in various aspects. As an example, physical fitness decreases risk of diseases, helps avoid injury, and improves life quality. Body flexibility, muscular strength, baseline metabolic rate, cardiovascular endurance, and body fat ratio are exemplary indexes of physical fitness. Physical exercises play a significant role in maintaining and improving a person's physical fitness. Physical exercises also work in alleviating work or life-related stress. As an example, weight training specifically provides many functional benefits; it strengths muscles to improve posture and provide better support for joints. Furthermore, weight training increases muscle mass, which in turn induces elevation in the baseline metabolism; a higher rate promotes long-term fat loss and lowering risk of chronic obesity-related diseases.

SUMMARY OF THE INVENTION

Physical exercises are well known to be beneficial to a person's physical wellbeing. However, physical exercises may work against a person's health if it is not performed at an appropriate intensity, amount, and duration. Furthermore, if physical exercises are not carried out correctly, unwanted injuries may occur. Traditional physical equipment may provide some information related to the intensity, amount, and duration of the activities, but such information is limited to a small number of activities. Personal trainers provide feedback and training for certain number of exercises; however, they can be less affordable and inconvenient for a daily routine.

One advantage of the devices, platforms, and media described herein is that they provide means to conveniently recognize, monitor, and record various physical activities. With its learning capabilities, new types of physical activities are easily added and stored for future work outs and learning. Thus users can choose from a wide range of physical activities to be monitored and tracked. Further, physiological parameters of a user are monitored simultaneously while exercising so that physical exercises are carried out with optimal intensity, amount, and duration for individual users. Another important advantage is that the users' performance is quantitatively compared to an expert and feedback is provided to promote effective learning and improvement in the performance. As a whole, the devices, platforms, and media described herein enable efficient learning with feedback, sensitive monitoring, storing, and easy recognition of physical exercises.

In one aspect, described herein are personal computing devices comprising: a processor, an onboard memory, an accelerometer, a gyroscope, and a display; a computer program including instructions executable by the digital processing device to create an exercise analysis application comprising: a software module configured to receive acceleration data from the accelerometer and angular velocity data from the gyroscope, the acceleration data and the angular velocity data associated with the bodily motion of a user in three dimensions; a software module configured to place the device in a learning mode, the learning mode comprising recording the acceleration data and the angular velocity data of the user performing a defined exercise to generate a statistical exercise model for the exercise; a software module configured to place the device in a normal mode, the normal mode comprising applying a probabilistic analysis to the acceleration data and the angular velocity data to identify an exercise event, classify the exercise by comparison to a recorded exercise model, and identify repetitions of the exercise; and a software module configured to apply a statistical analysis to the acceleration data and the angular velocity data to score the user's exercise form. In some embodiments, the device is adapted to be user-wearable. In further embodiments, the device is adapted to be wrist-wearable by the user. In further embodiments, the device comprises a wearable adapter, the wearable adapter reversibly connectable from the device to form a modular design. In some embodiments, the processor configured to an exercise analysis application further comprises a software module for further comprising a biosensor to measure a physiological parameter of the user. In further embodiments, the biosensor is selected from the group consisting of: a heart rate monitor, a thermometer, a respirometer, a glucose monitor, an electrolyte sensor, and an electrical conductance meter. In further embodiments, the biosensor is an optical biosensor. In further embodiments, the physiological parameter is selected from the group consisting of: heart rate, skin temperature, breathing rate, galvanic skin response, and hydration. In further embodiments, the application further comprises a software module configured to present a graphic user interface comprising a heart rate-based rest timer. In some embodiments, the personal computing device further comprises a geolocation element. In some embodiments, the device further comprises a wireless communications element. In further embodiments, the wireless communications element is a Bluetooth module or an ANT+ module. In some embodiments, the probabilistic analysis to classify the exercise comprises utilization of a neural network, context tree weighting, hidden markov models, or a combination thereof. In some embodiments, the score is derived, at least in part, from the user's body stability, the user's motion consistency, or a combination thereof. In some embodiments, the score is derived, at least in part, from comparison of the acceleration data and the angular velocity data to an exercise model generated from other users' data. In some embodiments, the score is derived, at least in part, from comparison of the acceleration data and the angular velocity data to an exercise model generated from one or more qualified fitness professionals. In some embodiments, the exercise is a unilateral weight training exercise or a bilateral weight training exercise. In some embodiments, the application further comprises a software module configured to present a user interface on the display, the user interface comprising the score, the exercise, the repetitions, exercise-specific messages, or a combination thereof. In further embodiments, the exercise is a weight training exercise and the exercise-specific messages are suggestions selected from the group consisting of: weight too heavy, weight too light, weight changed too much, motion too fast, body too unstable, form incorrect, form too inconsistent, and corrective advice regarding form.

In another aspect, described herein are exercise analysis platforms comprising: a personal computing device comprising a processor, an onboard memory, an accelerometer, a gyroscope, a display, and a communications element, the device configured to provide an personal exercise analysis application comprising: a software module configured to receive acceleration data from the accelerometer and angular velocity data from the gyroscope, the acceleration data and the angular velocity data associated with the bodily motion of a user in three dimensions; a software module configured to transmit the acceleration data and angular velocity data to an exercise analysis server application; a server processor configured to provide an exercise analysis server application comprising: a database of statistical exercise models, the exercise models generated from acceleration data and angular velocity data of a user performing a defined exercise; a software module configured to receive acceleration data and angular velocity data from the personal computing device; a software module configured to apply a probabilistic analysis to the acceleration data and the angular velocity data to identify an exercise event, classify the exercise by comparison to one or more of the statistical exercise models, and identify repetitions of the exercise; a software module configured to apply a statistical analysis to the acceleration data and the angular velocity data to score the user's exercise form. In some embodiments, the platform comprises at least 100, at least 1000, or at least 10,000 personal computing devices. In some embodiments, the personal exercise analysis application further comprises a software module configured to place the personal computing device in a learning mode, the learning mode comprising recording the acceleration data and the angular velocity data of the user performing a defined exercise to generate a statistical exercise model for the exercise. In some embodiments, the database of statistical exercise models comprises at least 10, at least 50, at least 100, or at least 500 exercise models, each exercise model associated with a particular exercise. In some embodiments, each exercise model is generated from averaged data from a plurality of users performing a defined exercise. In further embodiments, the average is a weighted average based on the level of expertise of each user. In some embodiments, one or more exercise models are generated from data from one or more qualified fitness professionals performing a defined exercise. In further embodiments, one or more exercise models is generated from data from a qualified fitness professional performing a defined exercise incorrectly to mimic common exercise form problems. In further embodiments, one or more exercise models is generated from data from a qualified fitness professional performing a defined exercise correctly to illustrate exemplary exercise form. In some embodiments, the personal computing device is adapted to be user-wearable. In some embodiments, the personal computing device is adapted to be wrist-wearable by the user. In further embodiments, the personal computing device comprises a wearable adapter, the wearable adapter reversibly connectable from the personal computing device to form a modular design. In some embodiments, the personal computing device further comprises a biosensor to measure a physiological parameter of the user. In further embodiments, the biosensor is selected from the group consisting of: a heart rate monitor, a thermometer, a respirometer, a glucose monitor, an electrolyte sensor, and an electrical conductance meter. In further embodiments, the biosensor is an optical biosensor. In further embodiments, the physiological parameter is selected from the group consisting of: heart rate, skin temperature, breathing rate, galvanic skin response, and hydration. In further embodiments, the personal exercise analysis application or the server application further comprises a software module configured to present a graphic user interface comprising a heart rate-based rest timer. In some embodiments, the personal computing device further comprises a geolocation element. In some embodiments, the communications element is a wireless communications element. In further embodiments, the wireless communications element is a Bluetooth module or an ANT+ module. In some embodiments, the probabilistic analysis to classify the exercise comprises utilization of a neural network, context tree weighting, hidden markov models, or a combination thereof. In some embodiments, the score is derived, at least in part, from the user's body stability, the user's motion consistency, or a combination thereof. In some embodiments, the score is derived, at least in part, from comparison of the acceleration data and the angular velocity data to an exercise model generated by a qualified fitness professional. In some embodiments, the exercise is a unilateral weight training exercise or a bilateral weight training exercise. In some embodiments, the personal exercise analysis application or the server application further comprises a software module configured to present a user interface on the display of the personal computing device, the user interface comprising the score, the exercise, the repetitions, exercise-specific messages, or a combination thereof. In further embodiments, the exercise is a weight training exercise and the exercise-specific messages are suggestions selected from the group consisting of: weight too heavy, weight too light, weight changed too much, motion too fast, body too unstable, form incorrect, form too inconsistent, and corrective advice regarding form. In some embodiments, the transmission of the acceleration data and angular velocity data to an exercise analysis server application is direct. In some embodiments, the transmission of the acceleration data and angular velocity data to an exercise analysis server application is indirect, the data first transmitted to a local device. In some embodiments, the personal exercise analysis application or the server application further comprises a software module configured to present an interface allowing the user to create a personal profile, the profile comprising weight, height, gender, wingspan, and fitness expertise.

In another aspects, disclosed herein are non-transitory computer-readable storage media encoded with instructions executable by a processor to perform personal exercise analysis, the instructions comprising: a software module configured to receive data from a personal computing device comprising an accelerometer and a gyroscope, the data comprising acceleration data from the accelerometer and angular velocity data from the gyroscope, the acceleration data and the angular velocity data associated with the bodily motion of a user in three dimensions; a software module configured to place the device in a learning mode, the learning mode comprising recording the acceleration data and the angular velocity data of the user performing a defined exercise to generate a statistical exercise model for the exercise; a software module configured to place the device in a normal mode, the normal mode comprising applying a probabilistic analysis to the acceleration data and the angular velocity data to identify an exercise event, classify the exercise by comparison to a recorded exercise model, and identify repetitions of the exercise; and a software module configured to apply a statistical analysis to the acceleration data and the angular velocity data to score the user's exercise form. In some embodiments, the personal computing device is adapted to be user-wearable. In some embodiments, the personal computing device is adapted to be wrist-wearable by the user. In further embodiments, the personal computing device comprises a wearable adapter, the wearable adapter reversibly connectable from the personal computing device to form a modular design. In some embodiments, the personal computing device further comprises a biosensor to measure a physiological parameter of the user. In further embodiments, the biosensor is selected from the group consisting of: a heart rate monitor, a thermometer, a respirometer, a glucose monitor, an electrolyte sensor, and an electrical conductance meter. In further embodiments, the biosensor is an optical biosensor. In further embodiments, the physiological parameter is selected from the group consisting of: heart rate, skin temperature, breathing rate, galvanic skin response, and hydration. In further embodiments, the processor configured to perform personal exercise analysis further comprises a software module configured to present a graphic user interface comprising a heart rate-based rest timer. In some embodiments, the personal computing device further comprises a geolocation element. In some embodiments, the personal computing device further comprises a wireless communications element. In further embodiments, the wireless communications element is a Bluetooth module or an ANT+ module. In some embodiments, the probabilistic analysis to classify the exercise comprises utilization of a neural network, context tree weighting, hidden markov models, or a combination thereof. In some embodiments, the score is derived, at least in part, from the user's body stability, the user's motion consistency, or a combination thereof. In some embodiments, the score is derived, at least in part, from comparison of the acceleration data and the angular velocity data to an exercise model generated from other users' data. In some embodiments, the score is derived, at least in part, from comparison of the acceleration data and the angular velocity data to an exercise model generated from one or more qualified fitness professionals. In some embodiments, the exercise is a unilateral weight training exercise or a bilateral weight training exercise. In some embodiments, the media further comprises a software module configured to present a user interface on the display, the user interface comprising the score, the exercise, the repetitions, exercise-specific messages, or a combination thereof. In further embodiments, the exercise is a weight training exercise and the exercise-specific messages are suggestions selected from the group consisting of: weight too heavy, weight too light, weight changed too much, motion too fast, body too unstable, form incorrect, form too inconsistent, and corrective advice regarding form.

In another aspects, described herein are non-transitory computer-readable storage media encoded with a computer program including instructions executable by a processor to create an exercise analysis server application comprising: a database of statistical exercise models, the exercise models generated from acceleration data and angular velocity data transmitted by a personal computing device associated with a user performing a defined exercise, the acceleration data and the angular velocity data each comprising data for X, Y, and Z-axes, the device in a learning mode; a software module configured to receive acceleration data and angular velocity data transmitted by a personal computing device associated with a user performing a defined exercise, the device in a normal mode; a software module configured to apply a probabilistic analysis to the received acceleration data and angular velocity data to identify an exercise event, classify the exercise by comparison to one or more of the statistical exercise models, and identify repetitions of the exercise; a software module configured to apply a statistical analysis to the received acceleration data and angular velocity data to score the user's exercise form. In some embodiments, data transmitted to the database are from at least 100, at least 1000, or at least 1000 wearable device. In some embodiments, the database of statistical exercise models comprises at least 10, at least 50, at least 100, or at least 500 exercise models, each exercise model associated with a particular exercise. In certain embodiments, the personal computing device comprises a processor, an onboard memory, an accelerometer, and a display. The personal computing device further comprises a gyroscope, a magnetometer, or an altimeter. In certain embodiments, the activity analysis server application further comprises a software module to receive data from a personal computing device, wherein the data are transmitted from accelerometer, a gyroscope, a magnetometer, or an altimeter to the personal computing device. In some embodiments, the personal activity server application receives data from at least 100, at least 1000, or at least 10,000 personal computing devices. In some embodiments, the personal activity analysis application further comprises a software module configured to place the personal computing device in a learning mode, the learning mode comprising recording the acceleration data of the user performing a defined activity to generate a statistical activity model for the activity. In some embodiments, each exercise model is generated from averaged data from a plurality of users performing a defined exercise. In some embodiments, the average is a weighted average based on the level of expertise of each user. In some embodiments, one or more exercise models are generated from data from one or more qualified fitness professionals performing a defined exercise. In further embodiments, one or more exercise models is generated from data from a qualified fitness professional performing a defined exercise incorrectly to mimic common exercise form problems. In further embodiments, one or more exercise models is generated from data from a qualified fitness professional performing a defined exercise correctly to illustrate exemplary exercise form. In some embodiments, the personal computing device is adapted to be user-wearable. In some embodiments, the personal computing device is adapted to be wrist-wearable by the user. In further embodiments, the personal computing device comprises a wearable adapter, the wearable adapter reversibly connectable from the personal computing device to form a modular design. In some embodiments, the personal computing device further comprises a biosensor to measure a physiological parameter of the user. In further embodiments, the biosensor is selected from the group consisting of: a heart rate monitor, a thermometer, a respirometer, a glucose monitor, an electrolyte sensor, and an electrical conductance meter. In further embodiments, the biosensor is an optical biosensor. In further embodiments, the physiological parameter is selected from the group consisting of: heart rate, skin temperature, breathing rate, galvanic skin response, and hydration. In further embodiments, the exercise analysis server application further comprises a software module configured to present a graphic user interface comprising a heart rate-based rest timer. In some embodiments, the personal computing device further comprises a geolocation element. In some embodiments, the probabilistic analysis to classify the exercise comprises utilization of a neural network, context tree weighting, hidden markov models, or a combination thereof. In some embodiments, the score is derived, at least in part, from the user's body stability, the user's motion consistency, or a combination thereof. In some embodiments, the score is derived, at least in part, from comparison of the acceleration data and the angular velocity data to an exercise model generated by a qualified fitness professional. In some embodiments, the exercise is a unilateral weight training exercise or a bilateral weight training exercise. In some embodiments, the exercise analysis server application further comprises a software module configured to present a user interface on the display of the personal computing device, the user interface comprising the score, the exercise, the repetitions, exercise-specific messages, or a combination thereof. In further embodiments, the exercise is a weight training exercise and the exercise-specific messages are suggestions selected from the group consisting of: weight too heavy, weight too light, weight changed too much, motion too fast, body too unstable, form incorrect, form too inconsistent, and corrective advice regarding form. In some embodiments, the transmission of the acceleration data and angular velocity data to the exercise analysis server application is direct. In some embodiments, the transmission of the acceleration data and angular velocity data to the exercise server application is indirect, the data first transmitted to a local device. In some embodiments, the exercise analysis server application further comprises a software module configured to present an interface allowing the user to create a personal profile, the profile comprising weight, height, gender, wingspan, and fitness expertise.

In another aspect, described herein are personal computing devices comprising: a processor, an onboard memory, an accelerometer, and a display; a computer program including instructions executable by the digital processing device to create an activity analysis application comprising: a software module configured to receive acceleration data from the accelerometer, the acceleration data associated with the bodily motion of a user in three dimensions; a software module configured to place the device in a learning mode, the learning mode comprising recording the acceleration data of the user performing a defined activity to generate a statistical activity model for the activity; a software module configured to place the device in a normal mode, the normal mode comprising applying a probabilistic analysis to the acceleration data to identify an activity event, classify the activity by comparison to a recorded activity model, and identify repetitions of the activity; and a software module configured to apply a statistical analysis to the acceleration data to score the user's activity form. In certain embodiments, the device further comprises a gyroscope, a magnetometer, or an altimeter. In certain embodiments, the activity analysis application further comprises a software module to receive data from a gyroscope, a magnetometer, or an altimeter. In certain embodiments, the device is adapted to be user-wearable. In further embodiments, the device is adapted to be wrist-wearable by the user. In further embodiments, the device comprises a wearable adapter, the wearable adapter reversibly connectable from the device to form a modular design. In some embodiments, the device further comprises a biosensor to measure a physiological parameter of the user. In further embodiments, the biosensor is selected from the group consisting of: a heart rate monitor, a thermometer, a respirometer, a glucose monitor, an electrolyte sensor, and an electrical conductance meter. In further embodiments, the biosensor is an optical biosensor. In further embodiments, the physiological parameter is selected from the group consisting of: heart rate, skin temperature, breathing rate, galvanic skin response, and hydration. In further embodiments, the application further comprises a software module configured to present a graphic user interface comprising a rest timer. In some embodiments, the device further comprises a geolocation element. In some embodiments, the device further comprises a wireless communications element. In further embodiments, the wireless communications element is a Bluetooth module or an ANT+ module. In certain embodiments, the probabilistic analysis to classify the activity comprises utilization of a neural network, context tree weighting, hidden markov models, or a combination thereof. In certain embodiments, the score is derived, at least in part, from the user's body stability, the user's motion consistency, or a combination thereof. In certain embodiments, the score is derived, at least in part, from comparison of the acceleration data to an activity model generated from other users' data. In certain embodiments, the score is derived, at least in part, from comparison of the acceleration data to an activity model generated from one or more qualified fitness professionals. In certain embodiments, the activity is a unilateral weight training activity or a bilateral weight training activity. In certain embodiments, the application further comprises a software module configured to present a user interface on the display, the user interface comprising the score, the activity, the repetitions, activity-specific messages, or a combination thereof. In further embodiments, the activity is a weight training activity and the activity-specific messages are suggestions selected from the group consisting of: weight too heavy, weight too light, weight changed too much, motion too fast, body too unstable, form incorrect, form too inconsistent, and corrective advice regarding form.

In another aspect, described herein are activity analysis platforms comprising: a personal computing device comprising a processor, an onboard memory, an accelerometer, a display, and a communications element, the device configured to provide an personal activity analysis application comprising: a software module configured to receive acceleration data from the accelerometer, the acceleration data associated with the bodily motion of a user in three dimensions; a software module configured to transmit the acceleration data to an activity analysis server application; a server processor configured to provide an activity analysis server application comprising: a database of statistical activity models, the activity models generated from acceleration data of a user performing a defined activity; a software module configured to receive acceleration data from the personal computing device; a software module configured to apply a probabilistic analysis to the acceleration data to identify an activity event, classify the activity by comparison to one or more of the statistical activity models, and identify repetitions of the activity; a software module configured to apply a statistical analysis to the acceleration data to score the user's activity form. In certain embodiments, the personal computing device further comprises a gyroscope, a magnetometer, or an altimeter. In certain embodiments, the activity analysis application further comprises a software module to receive data from a gyroscope, a magnetometer, or an altimeter. In some embodiments, the platform further comprises at least 100, at least 1000, or at least 10,000 personal computing devices. In some embodiments, the personal activity analysis application further comprises a software module configured to place the personal computing device in a learning mode, the learning mode comprising recording the acceleration data of the user performing a defined activity to generate a statistical activity model for the activity. In some embodiments, the database of statistical activity models comprises at least 10, at least 50, at least 100, or at least 500 activity models, each activity model associated with a particular activity. In some embodiments, each activity model is generated from averaged data from a plurality of users performing a defined activity. In further embodiments, the average is a weighted average based on the level of expertise of each user. In some embodiments, one or more activity models are generated from data from one or more qualified fitness professionals performing a defined activity. In further embodiments, one or more activity models are generated from data from a qualified fitness professional performing a defined activity incorrectly to mimic common activity form problems. In further embodiments, one or more activity models are generated from data from a qualified fitness professional performing a defined activity correctly to illustrate exemplary activity form. In some embodiments, the personal computing device is adapted to be user-wearable. In further embodiments, the personal computing device is adapted to be wrist-wearable by the user. In further embodiments, the personal computing device comprises a wearable adapter, the wearable adapter reversibly connectable from the personal computing device to form a modular design. In some embodiments, the personal computing device further comprises a biosensor to measure a physiological parameter of the user. In further embodiments, the biosensor is selected from the group consisting of: a heart rate monitor, a thermometer, a respirometer, a glucose monitor, an electrolyte sensor, and an electrical conductance meter. In further embodiments, the biosensor is an optical biosensor. In further embodiments, the physiological parameter is selected from the group consisting of: heart rate, skin temperature, breathing rate, galvanic skin response, and hydration. In further embodiments, personal activity analysis application or the server application further comprises a software module configured to present a graphic user interface comprising a timer. In some embodiments, the personal computing device further comprises a geolocation element. In some embodiments, the communications element is a wireless communications element. In further embodiments, the wireless communications element is a Bluetooth module or an ANT+ module. In some embodiments, the probabilistic analysis to classify the activity comprises utilization of a neural network, context tree weighting, hidden markov models, or a combination thereof. In some embodiments, the score is derived, at least in part, from the user's body stability, the user's motion consistency, or a combination thereof. In some embodiments, the score is derived, at least in part, from comparison of the acceleration data to an activity model generated by a qualified fitness professional. In some embodiments, the activity is a unilateral weight training activity or a bilateral weight training activity. In some embodiments, the personal activity analysis application or the server application further comprises a software module configured to present a user interface on the display of the personal computing device, the user interface comprising the score, the activity, the repetitions, activity-specific messages, or a combination thereof. In further embodiments, the activity is a weight training activity and the activity-specific messages are suggestions selected from the group consisting of: weight too heavy, weight too light, weight changed too much, motion too fast, body too unstable, form incorrect, form too inconsistent, and corrective advice regarding form. In some embodiments, the transmission of the acceleration data to an activity analysis server application is direct. In some embodiments, the transmission of the acceleration data to an activity analysis server application is indirect, the data first transmitted to a local device. In some embodiments, the personal activity analysis application or the server application further comprises a software module configured to present an interface allowing the user to create a personal profile, the profile comprising weight, height, gender, wingspan, and fitness expertise.

In another aspect, described herein are non-transitory computer-readable storage media encoded with instructions executable by a processor to perform personal activity analysis, the instructions comprising: a software module configured to receive data from a personal computing device comprising an accelerometer, the data comprising acceleration data from the accelerometer, the acceleration data associated with the bodily motion of a user in three dimensions; a software module configured to place the device in a learning mode, the learning mode comprising recording the acceleration data of the user performing a defined activity to generate a statistical activity model for the activity; a software module configured to place the device in a normal mode, the normal mode comprising applying a probabilistic analysis to the acceleration data to identify an activity event, classify the activity by comparison to a recorded activity model, and identify repetitions of the activity; and a software module configured to apply a statistical analysis to the acceleration data to score the user's activity form. In certain embodiments, the personal computing device comprises a processor, an onboard memory, an accelerometer, and a display. In some embodiments, the personal computing device further comprises a gyroscope, a magnetometer, or an altimeter. In certain embodiments, the activity analysis application further comprises a software module to receive data from a gyroscope, a magnetometer, or an altimeter. In certain embodiments, the personal computing device is adapted to be user-wearable. In further embodiments, the personal computing device is adapted to be wrist-wearable by the user. In further embodiments, the personal computing device comprises a wearable adapter, the wearable adapter reversibly connectable from the personal computing device to form a modular design. In some embodiments, the personal computing device further comprises a biosensor to measure a physiological parameter of the user. In further embodiments, the biosensor is selected from the group consisting of: a heart rate monitor, a thermometer, a respirometer, a glucose monitor, an electrolyte sensor, and an electrical conductance meter. In further embodiments, the biosensor is an optical biosensor. In further embodiments, the physiological parameter is selected from the group consisting of: heart rate, skin temperature, breathing rate, galvanic skin response, and hydration. In further embodiments, the media further comprises a software module configured to present a graphic user interface comprising a rest timer. In some embodiments, the personal computing device further comprises a geolocation element. In some embodiments, the personal computing device further comprises a wireless communications element. In further embodiments, the wireless communications element is a Bluetooth module or an ANT+ module. In certain embodiments, the probabilistic analysis to classify the activity comprises utilization of a neural network, context tree weighting, hidden markov models, or a combination thereof. In certain embodiments, the score is derived, at least in part, from the user's body stability, the user's motion consistency, or a combination thereof. In certain embodiments, the score is derived, at least in part, from comparison of the acceleration data to an activity model generated from other users' data. In certain embodiments, the score is derived, at least in part, from comparison of the acceleration data to an activity model generated from one or more qualified fitness professionals. In certain embodiments, the activity is a unilateral weight training activity or a bilateral weight training activity. In certain embodiments, the media further comprises a software module configured to present a user interface on the display, the user interface comprising the score, the activity, the repetitions, activity-specific messages, or a combination thereof. In further embodiments, the activity is a weight training activity and the activity-specific messages are suggestions selected from the group consisting of: weight too heavy, weight too light, weight changed too much, motion too fast, body too unstable, form incorrect, form too inconsistent, and corrective advice regarding form.

In another aspect, described herein are non-transitory computer-readable storage media encoded with a computer program including instructions executable by a processor to create an activity analysis server application comprising: a database of statistical activity models, the activity models generated from acceleration data transmitted by a personal computing device associated with a user performing a defined activity, the acceleration data comprising data for X, Y, and Z-axes, the device in a learning mode; a software module configured to receive acceleration data transmitted by a personal computing device associated with a user performing a defined activity, the device in a normal mode; a software module configured to apply a probabilistic analysis to the received acceleration data to identify an activity event, classify the activity by comparison to one or more of the statistical activity models, and identify repetitions of the activity; a software module configured to apply a statistical analysis to the received acceleration data to score the user's activity form. In certain embodiments, the personal computing device comprises a processor, an onboard memory, an accelerometer, and a display. The personal computing device further comprises a gyroscope, a magnetometer, or an altimeter. In certain embodiments, the activity analysis server application further comprises a software module to receive data from a personal computing device, wherein the data are transmitted from accelerometer, a gyroscope, a magnetometer, or an altimeter to the personal computing device. In some embodiments, the personal activity server application receives data from at least 100, at least 1000, or at least 10,000 personal computing devices. In some embodiments, the personal activity analysis application further comprises a software module configured to place the personal computing device in a learning mode, the learning mode comprising recording the acceleration data of the user performing a defined activity to generate a statistical activity model for the activity. In some embodiments, the database of statistical activity models comprises at least 10, at least 50, at least 100, or at least 500 activity models, each activity model associated with a particular activity. In some embodiments, each activity model is generated from averaged data from a plurality of users performing a defined activity. In further embodiments, the average is a weighted average based on the level of expertise of each user. In some embodiments, one or more activity models are generated from data from one or more qualified fitness professionals performing a defined activity. In further embodiments, one or more activity models are generated from data from a qualified fitness professional performing a defined activity incorrectly to mimic common activity form problems. In further embodiments, one or more activity models are generated from data from a qualified fitness professional performing a defined activity correctly to illustrate exemplary activity form. In some embodiments, the personal computing device is adapted to be user-wearable. In further embodiments, the personal computing device is adapted to be wrist-wearable by the user. In further embodiments, the personal computing device comprises a wearable adapter, the wearable adapter reversibly connectable from the personal computing device to form a modular design. In some embodiments, the personal computing device further comprises a biosensor to measure a physiological parameter of the user. In further embodiments, the biosensor is selected from the group consisting of: a heart rate monitor, a thermometer, a respirometer, a glucose monitor, an electrolyte sensor, and an electrical conductance meter. In further embodiments, the biosensor is an optical biosensor. In further embodiments, the physiological parameter is selected from the group consisting of: heart rate, skin temperature, breathing rate, galvanic skin response, and hydration. In further embodiments, the personal activity analysis application or the server application further comprises a software module configured to present a graphic user interface comprising a timer. In some embodiments, the personal computing device further comprises a geolocation element. In some embodiments, the communications element is a wireless communications element. In further embodiments, the wireless communications element is a Bluetooth module or an ANT+ module. In some embodiments, the probabilistic analysis to classify the activity comprises utilization of a neural network, context tree weighting, hidden markov models, or a combination thereof. In some embodiments, the score is derived, at least in part, from the user's body stability, the user's motion consistency, or a combination thereof. In some embodiments, the score is derived, at least in part, from comparison of the acceleration data to an activity model generated by a qualified fitness professional. In some embodiments, the activity is a unilateral weight training activity or a bilateral weight training activity. In some embodiments, the personal activity analysis application or the server application further comprises a software module configured to present a user interface on the display of the personal computing device, the user interface comprising the score, the activity, the repetitions, activity-specific messages, or a combination thereof. In further embodiments, the activity is a weight training activity and the activity-specific messages are suggestions selected from the group consisting of: weight too heavy, weight too light, weight changed too much, motion too fast, body too unstable, form incorrect, form too inconsistent, and corrective advice regarding form. In some embodiments, the transmission of the acceleration data to an activity analysis server application is direct. In some embodiments, the transmission of the acceleration data to an activity analysis server application is indirect, the data first transmitted to a local device. In some embodiments, the personal activity analysis application or the server application further comprises a software module configured to present an interface allowing the user to create a personal profile, the profile comprising weight, height, gender, wingspan, and fitness expertise.

BRIEF DESCRIPTION OF THE DRAWINGS

FIG. 2A is a flow diagram of a method for the analyses of personal data as received by one embodiment of the present invention.

FIG. 6 is a side view of an exemplary embodiment of the personal computing device attached and detached from a wrist band.

DETAILED DESCRIPTION OF THE INVENTION

Figure 1A:
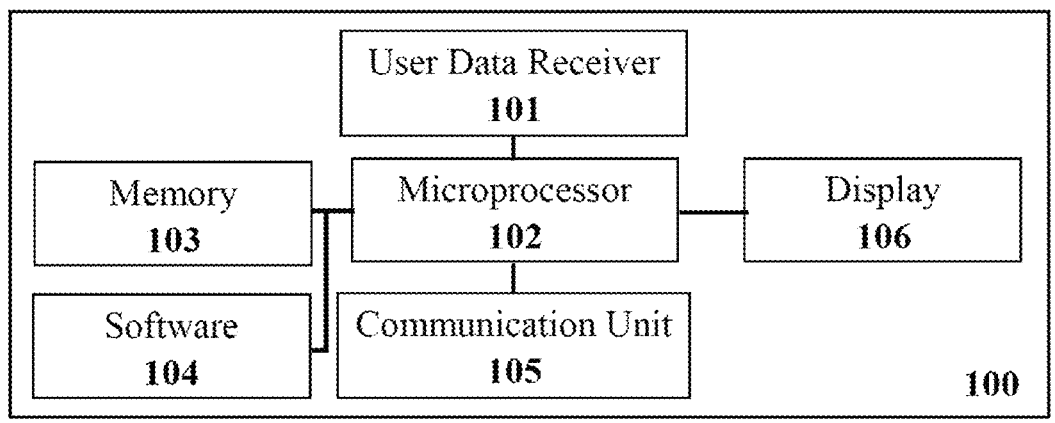
FIG. 1A is a block diagram of an exemplary embodiment of a system.

Physical exercises are well known to be beneficial to a person's physical wellbeing. However, physical exercises may work against a person's health if it is not performed at an appropriate intensity, amount, and duration. Furthermore, if physical exercises are not carried out correctly, unwanted injuries may occur. Traditional physical equipment may provide some information related to the intensity, amount, and duration of the activities, but such information is limited to a small number of activities. Personal trainers provide feedback and training to certain number of exercises, however, they can be less affordable and inconvenient for a daily routine.

One advantage of the devices, platforms, and media described herein is that they provide means to conveniently recognize, monitor, and record various physical activities. With its learning capabilities, new types of physical activities are easily added and stored for future working out and learning. Thus users can choose from a wide range of physical activities to be monitored and tracked. Further, physiological parameters of a user are monitored simultaneously while exercising so that physical exercises are carried out with optimal intensity, amount, and duration for individual users. Another important advantage is that the users' performance is quantitatively compared to an expert and feedback is provided to promote effective learning and improvement in the performance. As a whole, the devices, platforms, and media described herein enable efficient learning with feedback, sensitive monitoring, storing, and easy recognition of physical exercises.

Described herein, in certain embodiments, are personal computing devices comprising: a processor, an onboard memory, an accelerometer, a gyroscope, and a display; a computer program including instructions executable by the digital processing device to create an exercise analysis application comprising: a software module configured to receive acceleration data from the accelerometer and angular velocity data from the gyroscope, the acceleration data and the angular velocity data associated with the bodily motion of a user in three dimensions; a software module configured to place the device in a learning mode, the learning mode comprising recording the acceleration data and the angular velocity data of the user performing a defined exercise to generate a statistical exercise model for the exercise; a software module configured to place the device in a normal mode, the normal mode comprising applying a probabilistic analysis to the acceleration data and the angular velocity data to identify an exercise event, classify the exercise by comparison to a recorded exercise model, and identify repetitions of the exercise; and a software module configured to apply a statistical analysis to the acceleration data and the angular velocity data to score the user's exercise form.

Also described herein, in some embodiments, are exercise analysis platforms comprising: a personal computing device comprising a processor, an onboard memory, an accelerometer, a gyroscope, a display, and a communications element, the device configured to provide an personal exercise analysis application comprising: a software module configured to receive acceleration data from the accelerometer and angular velocity data from the gyroscope, the acceleration data and the angular velocity data associated with the bodily motion of a user in three dimensions; a software module configured to transmit the acceleration data and angular velocity data to an exercise analysis server application; a server processor configured to provide an exercise analysis server application comprising: a database of statistical exercise models, the exercise models generated from acceleration data and angular velocity data of a user performing a defined exercise; a software module configured to receive acceleration data and angular velocity data from the personal computing device; a software module configured to apply a probabilistic analysis to the acceleration data and the angular velocity data to identify an exercise event, classify the exercise by comparison to one or more of the statistical exercise models, and identify repetitions of the exercise; a software module configured to apply a statistical analysis to the acceleration data and the angular velocity data to score the user's exercise form.

Also disclosed herein, in certain embodiments, are non-transitory computer-readable storage media encoded with instructions executable by a processor to perform personal exercise analysis, the instructions comprising: a software module configured to receive data from a personal computing device comprising an accelerometer and a gyroscope, the data comprising acceleration data from the accelerometer and angular velocity data from the gyroscope, the acceleration data and the angular velocity data associated with the bodily motion of a user in three dimensions; a software module configured to place the device in a learning mode, the learning mode comprising recording the acceleration data and the angular velocity data of the user performing a defined exercise to generate a statistical exercise model for the exercise; a software module configured to place the device in a normal mode, the normal mode comprising applying a probabilistic analysis to the acceleration data and the angular velocity data to identify an exercise event, classify the exercise by comparison to a recorded exercise model, and identify repetitions of the exercise; and a software module configured to apply a statistical analysis to the acceleration data and the angular velocity data to score the user's exercise form.

Also described herein, in certain embodiments, are non-transitory computer-readable storage media encoded with a computer program including instructions executable by a processor to create an exercise analysis server application comprising: a database of statistical exercise models, the exercise models generated from acceleration data and angular velocity data transmitted by a personal computing device associated with a user performing a defined exercise, the acceleration data and the angular velocity data each comprising data for X, Y, and Z-axes, the device in a learning mode; a software module configured to receive acceleration data and angular velocity data transmitted by a personal computing device associated with a user performing a defined exercise, the device in a normal mode; a software module configured to apply a probabilistic analysis to the received acceleration data and angular velocity data to identify an exercise event, classify the exercise by comparison to one or more of the statistical exercise models, and identify repetitions of the exercise; a software module configured to apply a statistical analysis to the received acceleration data and angular velocity data to score the user's exercise form.

Also described herein, in certain embodiments, are personal computing devices comprising: a processor, an onboard memory, an accelerometer, and a display; a computer program including instructions executable by the digital processing device to create an activity analysis application comprising: a software module configured to receive acceleration data from the accelerometer, the acceleration data associated with the bodily motion of a user in three dimensions; a software module configured to place the device in a learning mode, the learning mode comprising recording the acceleration data of the user performing a defined activity to generate a statistical activity model for the activity; a software module configured to place the device in a normal mode, the normal mode comprising applying a probabilistic analysis to the acceleration data to identify an activity event, classify the activity by comparison to a recorded activity model, and identify repetitions of the activity; and a software module configured to apply a statistical analysis to the acceleration data to score the user's activity form.

Also described herein, in certain embodiments, are activity analysis platforms comprising: a personal computing device comprising a processor, an onboard memory, an accelerometer, a display, and a communications element, the device configured to provide an personal activity analysis application comprising: a software module configured to receive acceleration data from the accelerometer, the acceleration data associated with the bodily motion of a user in three dimensions; a software module configured to transmit the acceleration data to an activity analysis server application; a server processor configured to provide an activity analysis server application comprising: a database of statistical activity models, the activity models generated from acceleration data of a user performing a defined activity; a software module configured to receive acceleration data from the personal computing device; a software module configured to apply a probabilistic analysis to the acceleration data to identify an activity event, classify the activity by comparison to one or more of the statistical activity models, and identify repetitions of the activity; a software module configured to apply a statistical analysis to the acceleration data to score the user's activity form.

Also described herein, in certain embodiments, are non-transitory computer-readable storage media encoded with instructions executable by a processor to perform personal activity analysis, the instructions comprising: a software module configured to receive data from a personal computing device comprising an accelerometer, the data comprising acceleration data from the accelerometer, the acceleration data associated with the bodily motion of a user in three dimensions; a software module configured to place the device in a learning mode, the learning mode comprising recording the acceleration data of the user performing a defined activity to generate a statistical activity model for the activity; a software module configured to place the device in a normal mode, the normal mode comprising applying a probabilistic analysis to the acceleration data to identify an activity event, classify the activity by comparison to a recorded activity model, and identify repetitions of the activity; and a software module configured to apply a statistical analysis to the acceleration data to score the user's activity form.

Also described herein, in certain embodiments, are non-transitory computer-readable storage media encoded with a computer program including instructions executable by a processor to create an activity analysis server application comprising: a database of statistical activity models, the activity models generated from acceleration data transmitted by a personal computing device associated with a user performing a defined activity, the acceleration data comprising data for X, Y, and Z-axes, the device in a learning mode; a software module configured to receive acceleration data transmitted by a personal computing device associated with a user performing a defined activity, the device in a normal mode; a software module configured to apply a probabilistic analysis to the received acceleration data to identify an activity event, classify the activity by comparison to one or more of the statistical activity models, and identify repetitions of the activity; a software module configured to apply a statistical analysis to the received acceleration data to score the user's activity form.

Certain Terminologies

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Overview

The present invention relates to statistical analysis of three dimensional (3D) bodily motion data captured by motion sensors using a personal computing device. The personal exercise analysis application of the personal computing device is configured to collect 3D motion data captured from accelerometer and gyroscope, carry out statistical analysis of such data. The device is also configured to present exercise-related information and physiological information of a user on the display. Further, the present invention incorporates statistical models to recognize new exercises performed by the user. The present invention also incorporates analysis methods to compare exercises performed by the user with recorded exercises performed by a qualified fitness expertise to facilitate accurate and efficient learning.

Personal Computing Devices

In some embodiments, the devices, platforms, and media described herein include a personal computing device. In certain embodiments, the personal computing device includes a processor, a memory, an accelerometer, and a display. In some embodiments, the accelerometer measures the acceleration in one, two, or three spatial dimensions and/or one temporal dimension with positive and negative directions for any single dimension. In some embodiments, the personal computing device includes an accelerometer, a gyroscope, a magnetometer, or an altimeter. In some embodiments, the gyroscope measures orientation information in one, two, or three spatial dimensions and/or one temporal dimension with positive and negative directions for any single dimension. In some embodiments, the processor comprises one or more of a digital signal processor, a digital processor, a microprocessor, or an Application Specific Integrated Circuits (ASIC).

In some embodiment, the personal computing device includes an on-device display. In some embodiments, the display color, font, image size, contrast, or contents are user-selected. In some embodiments, the personal computing device optionally includes an audio indicator. In further embodiments, contents of the on-device display outputs into audio by user-selection.

In some embodiments, the personal computing device is user wearable. In further embodiments, the personal computing device is wrist wearable by the user. In other embodiments, the personal computing device can be attached to any skin area on the body. In some embodiments, the device comprises a wearable adapter that is reversibly connectable from the device to form a modular design. In some embodiments, the personal computing device is wearable around a shoulder, an ear, the neck, a finger, a palm, an ankle, the chest, an arm, the waist, a leg, a foot, or the torso. In some embodiments, the device comprises an adaptor that allows the device to be reversibly connected to gym equipment, an exercise apparatus, a sport gear, or the like. In further embodiments, the device is attached or reversibly connected to a dumbbell, a barbell, a rowing machine, a kayaking pedal, a baseball bat, a golf stick, a tennis racquet, a badminton racquet, a ping-pong paddle, a boxing glove, a piece of floor, a handle, a glove, a piece of clothes, a shoe, a belt, a seat, a arm-rest, a mat, or the like. In other embodiments, the device is reversibly connected to a mobile device, a computer, a GPSs, an iPad, a USB drive, a printer, a scanner, a TV, a sever, a car, a smart watch, a google glass, an iPod, a game player, a projector, a camera, or similar electronic devices.

In some embodiments, the device further comprises a biosensor to measure a physiological parameter of the user. In further embodiments, the biosensor is an optical, electrical, magnetic, electromagnetic, chemical, electrochemical, UV light, pressure, velocity, sound, thermal, or mechanical biosensor. In further embodiments, the biosensor comprises a heart rate monitor, thermometer, a respirometer, a blood glucose monitor, an electrolyte sensor, an electrical conductance meter, a blood pressure sensor, the blood oxygen sensor, the body fat sensor, a muscle sensor, an EMG electrode, an EEG sensor, a ECG electrode, the body hydration sensor, or the like. In some embodiments, the physiological parameter comprises heart rate, skin temperature, breathing rate, pulse, galvanic skin response, hydration, blood oxygen level, blood glucose level, body fat ratio, muscle fatigue level, EMG, EEG, ECG, or the like.

Referring to FIG. 6, in particular embodiment, the personal computing device is attached or detached from a wrist band via the wearable adaptor.

Figure 7:
FIG. 7 shows an indicating an exemplary embodiment of the personal computing device with images showing on-device displayed contents.

Referring to FIG. 7, in a particular embodiment, a personal computing device is attached to a wrist band and exemplary images of on-device display are shown. In this particular embodiment, the on-device display shows a device-start greeting of "Free Coach Home", and an exercise form recorded as "Routine 1" when a user is performing the corresponding exercise. The on-device display optionally shows a user-input body weight as part of a user profile. The on-device display optionally shows the exercise repetition number (REPS) and the physiological data of the user such as hear rate in beat per minute (BPM) when a user is performing an exercise.

In some embodiments, the device further comprises a software module configured to present a graphic user interface comprising a rest timer. In further embodiments, the rest timer is based on a physiological parameter selected from a heart rate, a skin temperature, a blood pressure, a blood oxygenation level, a blood glucose level, a breathing rate, a body hydration level, a galvanic skin response, a body fat ratio, an EMG signal, an EEG signal, an ECG signal, muscle fatigue level, or the like. In other embodiments, the rest timer is determined by exercise duration, calorie burned, exercise repetitions, exercise score, form error, or other exercise related events.

In some embodiments, the device further comprises a geolocation element, wherein the geolocation element identifies the geographical location of the personal computing device. In further embodiments, the geographical location comprises altitude, elevation, latitude, longitude, coordinates, atmospheric pressure, or the like.

In some embodiments, the device further comprises a wireless communication element, wherein the element allows wireless communication with fitness equipment, a computer, an exercise analysis server application, another personal computing device, a sport gear, or the like. In further embodiments, the wireless communication element is a Bluetooth module, an ANT+ module, a Wi-Fi module, an IEEE 802.15.4 microchip, a ZigBee module, a Wireless USB, an IrDA module, a ZWave module, a wireless network adapter, a wireless internet card, a body area network module, near field communication, or the like.

Personal Exercise Analysis Applications

In some embodiments, the devices, platforms, and media described herein include a personal exercise analysis application or use of the same. In certain embodiments, the personal exercise analysis application comprises a software module to receive data associated with a bodily motion of a user in three dimensions. In further embodiments, the data associated with a bodily motion of a user in three dimensions comprise acceleration data and/or angular velocity data. In yet further embodiments, the data associated with a bodily motion of a user in three dimensions are received from one or more selected from accelerometer or gyroscope. In other embodiments, the data associated with a bodily motion of a user in three dimensions are acceleration data. In further embodiments, the data associated with a bodily motion of a user in three dimensions are received from one or more of accelerometers. In some embodiments, acceleration data comprises acceleration information in one, two, or three spatial dimensions and/or one temporal dimension with positive and negative directions for any single dimension, or combinations thereof. In some embodiments, angular velocity data comprises orientation information in one, two, or three spatial dimensions and/or one temporal dimension with positive and negative directions for any single dimension, or combinations thereof. In some embodiments, acceleration data and angular velocity data are three by three vectors. In other embodiments, acceleration data and angular velocity data are four dimensional vectors. In yet further embodiments, the data associated with a bodily motion of a user in three dimensions are received from pressure sensor, GPS, timer, velocity sensor, vibration sensor, or thermometer. In some embodiment, the data associated with a bodily motion of a user in three dimensions comprises one, two, or three dimensional distance, displacement, acceleration, angular velocity, linear momentum, speed, coordinate, geolocation, force, torque, radius, circumference, altitude, duration, pressure, or the like. In further embodiments, the data associated with a bodily motion of a user in three dimensions comprises mathematical or statistical processing of one, two, or three dimensional distance, displacement, acceleration, angular velocity, linear momentum, speed, coordinate, geolocation, force, torque, radius, circumference, altitude, duration, pressure, or the like. In some embodiments, the data associated with a bodily motion of a user in three dimensions are further related to exercising environment, including atmospheric pressure, water resistance, wind resistance, water pressure, wind speed, water speed, gravity level, or temperature.

In certain embodiments, the personal exercise analysis application comprises a software module configured to place the personal computing device in a learning mode. In some embodiments, the learning mode comprises recording of data associated with the bodily motion of a user performing a defined exercise in one, two, or three dimensions. In further embodiments, the data associated with the bodily motion of a user in three dimensions are acceleration data and/or angular velocity data of the user performing a defined exercise in order to generate a statistical exercise model for the exercise. In some embodiments, the user is one or more of a qualified fitness professional, a coach, a personal trainer, an expert, an athlete, a professional player, a robot, or the like. In some embodiments, the exercise is a cardio, weight, strength, flexibility, or skill related exercise. In further embodiments, the exercise is a unilateral weight training exercise, a bilateral weight training exercise, a pushup exercise, a fly exercise, a dumbbell exercise, a pull-down exercise, a deadlift exercise, a barbell exercise, a pull-up exercise, a baseball exercise, a sit-up exercise, a curl exercise, a plank exercise, a crunch exercise, a bench press exercise, a push-down exercise, a floor press exercise, a tennis exercise, a golf exercise, a kayaking exercise, a badminton exercise, a ping-pong exercise, a swimming exercise, a boxing exercise, a bowling exercise, a dancing exercise, a yoga exercise, a pliates exercise, a rowing exercise, a running exercise, a jogging exercise, a hiking exercise, a climbing exercise, a skating exercise, a biking exercise, a hokey exercise, a fencing exercise, a surfing exercise, an archering exercise, a horse-riding exercise, a basketball shooting exercise, or the like. In further embodiments, statistical exercise model of a defined exercise are generated separately based on exercise type, age, body weight, height, gender, wingspan, repetition, or information of the like.

In some embodiments, each exercise model is generated from average data from one or more users performing a defined exercise. In further embodiments, the average data is a weighted average data based on the level of expertise of each user. In some embodiments, one or more exercise models are generated from data from one or more qualified fitness professionals performing a defined exercise. In some embodiments, one or more exercise models is generated from data from a qualified fitness professional performing a defined exercise incorrectly to mimic common exercise form problems. In other embodiments, one or more exercise models are generated from data from a qualified fitness professional performing a defined exercise correctly to illustrate exemplary exercise form. In other embodiments, each exercise model is generated from average data from a single user performing a defined exercise at multiple repetitions. In further embodiments, the statistical models are generated from 3D bodily motion of a user performing a defined exercise.

In some embodiments, the personal exercise analysis application further comprises a software module configured to place the device in a normal mode, the normal mode comprising applying a probabilistic analysis to data associated with a three-dimensional bodily motion to identify an exercise type, classify the exercise type by comparison to a recorded exercise model, and identify repetitions of the exercise. In some embodiments, the three dimensional bodily motion is raw motion related data collected from the personal computing device. In other embodiments, the 3D bodily motion related data are preprocessed based on raw data collected from motion sensors before the application of a probabilistic analysis. In further embodiments, the preprocessing comprises one or more of space, time, or frequency-related averaging, quantization, denoising, smoothing, linear or non-linear fitting, filtering, weighting, truncating, deleting, transforming, multiplying, subtracting, dividing, interpolating, derivating, rounding, reorganizing, squaring, exponentiation, or the like. In yet further embodiments, the preprocessing comprises mathematical or statistical operation of the raw data including calculating a standard score, a z-score, a quantization, a PCA analysis (principal component analysis), a subtraction of the mean of the raw data, a division by standard deviation of the raw data, or the like.

In some embodiments, the probabilistic analysis to classify the exercise comprises utilization of a neural network, a context tree weighting, a hidden markov model, a dynamic system, a principal component analysis, a k-mean clustering, a dynamic Bayesian network, a mixture model, a regression model, a markov random field, a conditional random field, a template matching, a dynamic probabilistic graphical model, a K-nearest neighbors model, a patent recognition model, a statistical learning model, a machine learning model, or combinations of the same. In some embodiments, the inputs to the probabilistic analysis include the unprocessed bodily motion data in one, two, or three dimensions of a user performing one or more defined exercises. In further embodiments, the inputs to the probabilistic analysis include the preprocessed bodily motion data in one, two, or three dimensions of a user performing one or more defined exercises. In further embodiments, the preprocessing is by mathematical or statistical operations. In some embodiments, the inputs to the probabilistic analysis comprise one or more recorded exercise models. In some embodiments, the outputs of the probabilistic analysis comprise probabilities, vector of probabilities, significance, vector of significance, p values, vector of p values, estimation error, vector of estimation errors, or the like. In further embodiments, the output values are greater than or equal to 0 and less or equal to 1. In further embodiments, the outputs of the probabilistic analysis have a fixed sum. In yet further embodiments, the outputs of the probabilistic analysis have a sum of 1.

In some embodiments, the personal exercise analysis application further comprises a software module configured to apply a comparison method to data of 3D bodily motion to score the user's exercise form. In further embodiments, the score comprises an average score, a personal highest score, a personal lowest score, a score profile over time, a score profile over repetition, or combinations of the like. The comparison method comprises a sum of squared difference, a statistical divergence, a root mean square deviation, a sum of root mean square deviation, a sum of root mean square, a regression, the Mahalanobis distance, or combinations of the like. In further embodiments, the user's exercise form are scored using a letter grade selecting from a list of A, B, C, D, E, and F. In other embodiments, the user's exercise form is scored using a percentile grade ranging from 100 percentile to 0 percentile. In other embodiments, the user's exercise form is scored using a numerical grade ranging from 10 to 0, 5 to 0, or 4 to 0. In some embodiments, the score is derived, at least in part, from the user's body stability, the user's motion consistency, the user's improvement over time or repetitions, or combinations of the same. In some embodiments, the score is derived, at least in part, from comparison of data of 3D bodily motion of the user to an exercise model generated from a different user or the average of at least two other users' data. In further embodiments, the different user or the other users are one or more qualified fitness professionals, a coach, a personal trainer, an expert, an athlete, a professional player, a robot, or the like.

In some embodiments, the application further comprises a software module configured to present a user interface, the user interface allow user-device interaction via an input device. In further embodiments, the input device comprises a touchscreen, a key, a button, a scroll, a mouse, a keyboard, a pointing device, a remote control, a microphone, a motion sensor, an eye movement sensor, a temperature sensor, an optical sensor, or a pressure sensor. In further embodiments, the interaction comprises a touch, a click, a vibration, a shake, a tap, highlighting, circling, contouring, a gesture, pointing, swiping, pressing, an eye movement, or crossing. In some embodiments, the user interface allow a user to create or select a content for on-device display, a device mode, a rest timer, an instantaneous feedback via sound, light, or vibration, a device calibration, a report of error, a correction of error, an exercise-related reminder, a physiological data-related reminder, or a combination thereof. In further embodiments, the instantaneous feedback via sound, light, or vibration comprises feedback of the physiological data of the user or the exercise-related performance of the user. In some embodiments, the on-device display comprises display of a score, an exercise type, a number of repetitions, level of muscle fatigue, exercise duration, an exercise-specific message, physiological data of the user, a device-specific message, or the like. In further embodiments, the graphic user interface allows a user to make a correction to exercise-related information and/or activity-related information with one or more mathematical or statistical operations. In further embodiments, the activity-related information includes an activity type, a number of repetitions, an activity log, a score, an average score, an average duration, an average weight, a total duration, a total score, a minimal or maximal score, a score log, a weight, a duration, or any activity-derived information. In further embodiments, a correction to exercise related information is used to update statistical analysis or probabilistic analysis.

In some embodiments, the exercise is a weight training exercise, and the exercise-specific message comprises: time spent, number of repetitions, weight too much, weight too litter, weight changed too much, motion too fast, body too unstable, form too incorrect, form too inconsistent, number of exercise stored, and corrective advice regarding exercise form. In some embodiments, the device-specific message comprises: Bluetooth connected, Bluetooth disconnected, total number of exercises stored, new exercise type added, exercise type deleted, exercise type error, low storage space, battery level notification, geolocation detected, reset timer started, reset timer stopped, geolocation error, environment detected, environment error, or combinations of the like.

Figure 3:
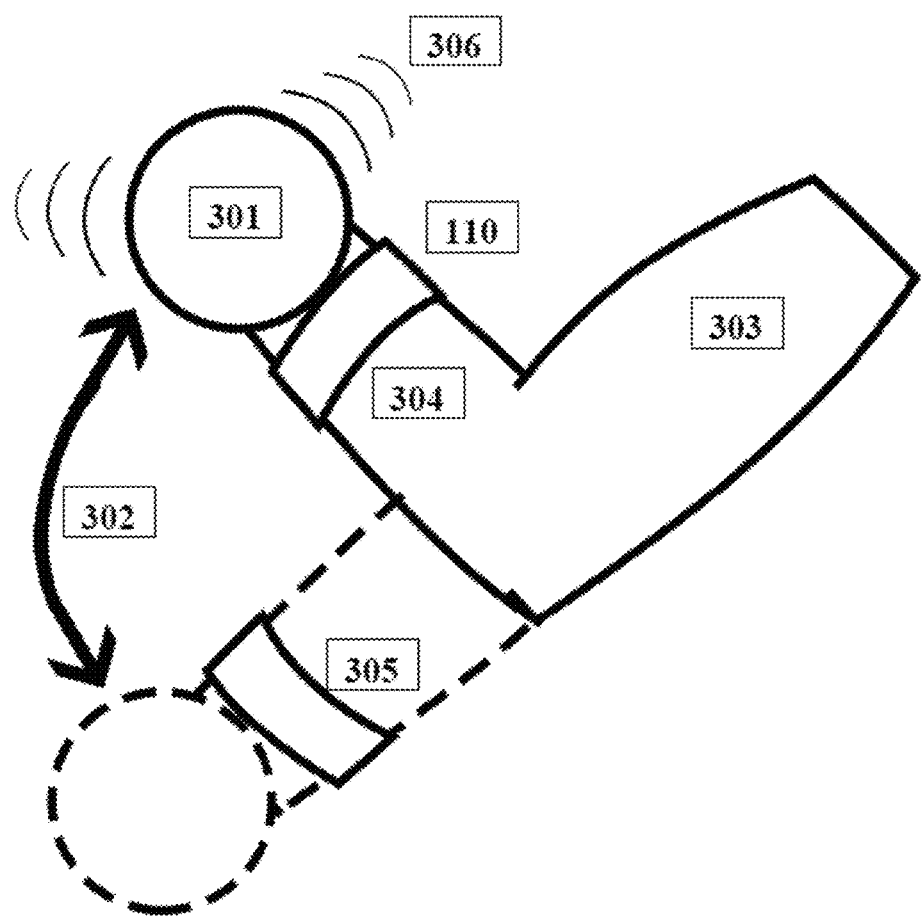
FIG. 3 is a schematic diagram of the device in the system of FIG. 1B.

FIG. 3 is a schematic diagram of the use of the system 110. The system 110 is worn by the user 303 on the arm 304. The user 303 is holding a weight 301 with which a fitness exercise 302 is being performed. The position of the system 130 on the arm 214 changes as the fitness exercise 302 is performed. Data about the user 303 and the position of the arm 304 can be detected by user data receivers 101. The microprocessor 102 can perform analyses of this data with the software 104 in order to determine the fitness exercise 302. The fitness exercise 302 performed can be stored in a memory 103, sent to a communication unit 105, and/or presented to the user 303 with a display 106. The user 303 can then input data 117 that the microprocessor 102 will use according to software 104 to adjust future computation instructions. The analyses 210 can also include counting repetitions and sets of different exercises.

Figure 4A:
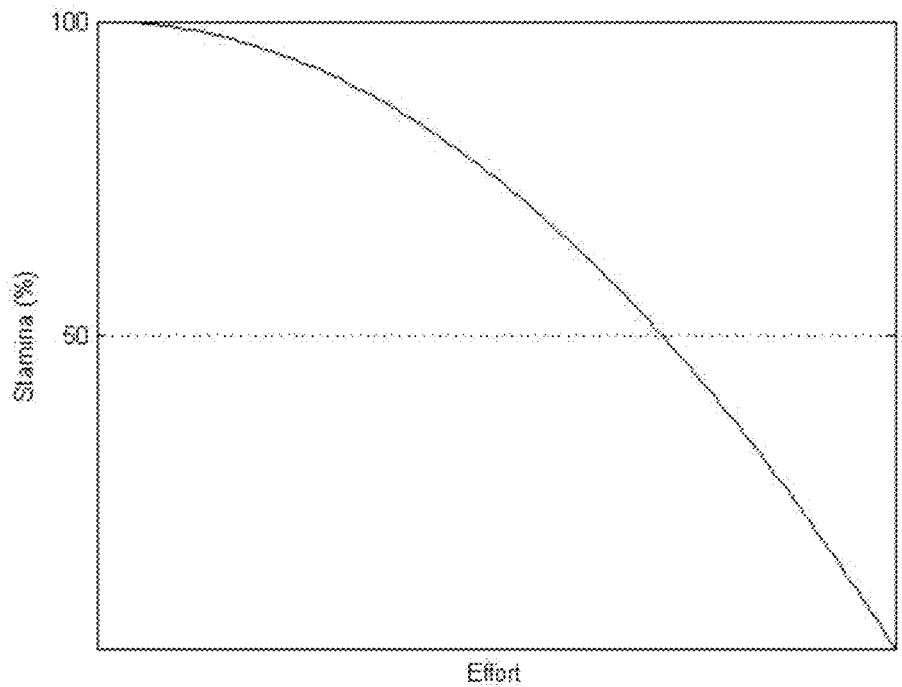
FIG. 4A is a graph indicating the effect of effort on stamina during exercise.

FIG. 4A is a graph that is indicative of the level of effort that the user 303 can produce while performing the fitness exercise 302. It demonstrates how fatigue can set to the user 303.

Figure 4B:
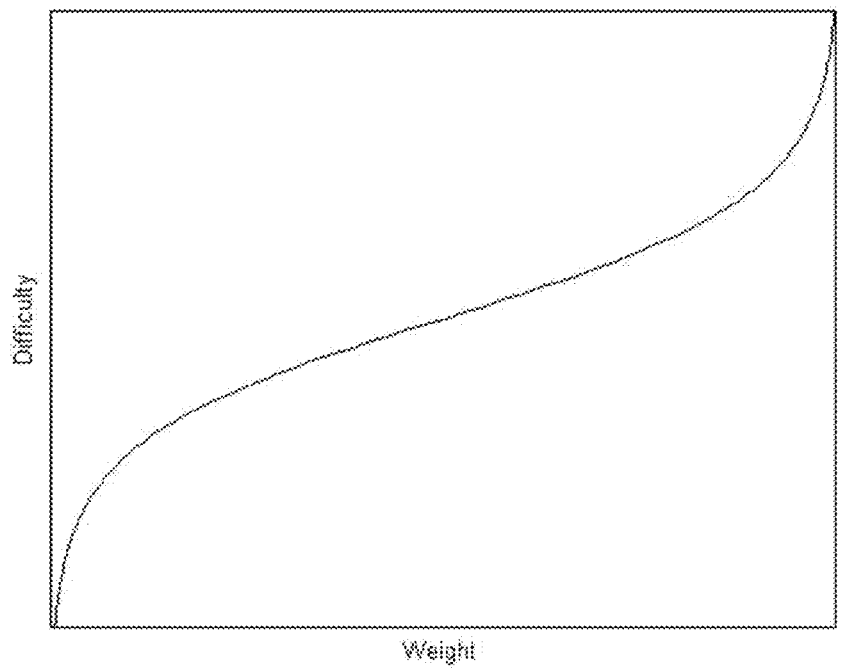
FIG. 4B is a graph indicating the effect of increasing resistance of an exercise on the difficulty performing said exercise.

FIG. 4B is a graph that is indicative of how resistance of exercise or the weight 301 affects the difficulty of performing an exercise 302 as perceived by the user 303.

Figure 5A:
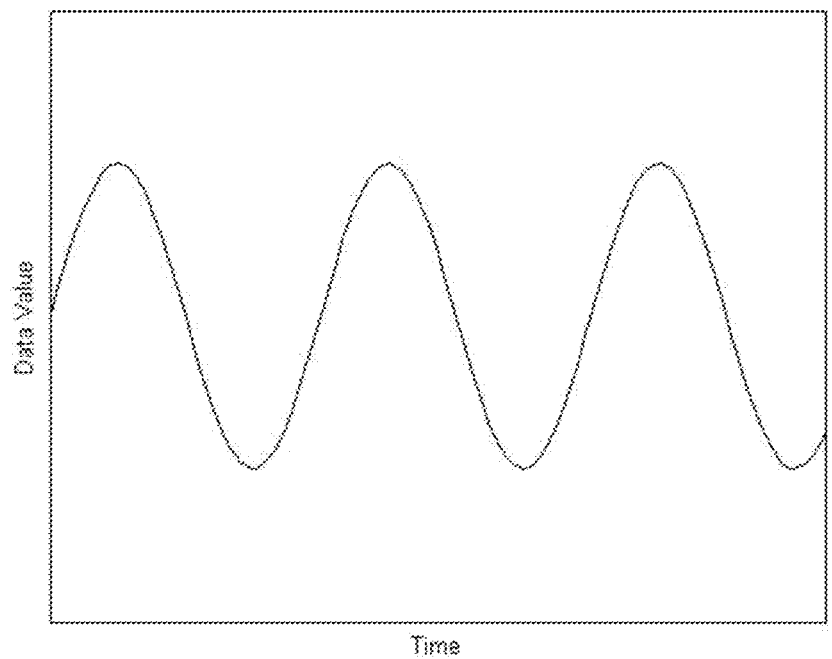
FIG. 5A is a graph indicating a data stream that the system of FIG. 1B may receive.

FIG. 5A demonstrates a data stream as received by the system 100 through the receiver 101 while the user 303 is performing an exercise 302 while not fatigued, or while performing with low resistance or performing with low weight 301.

Figure 5B:
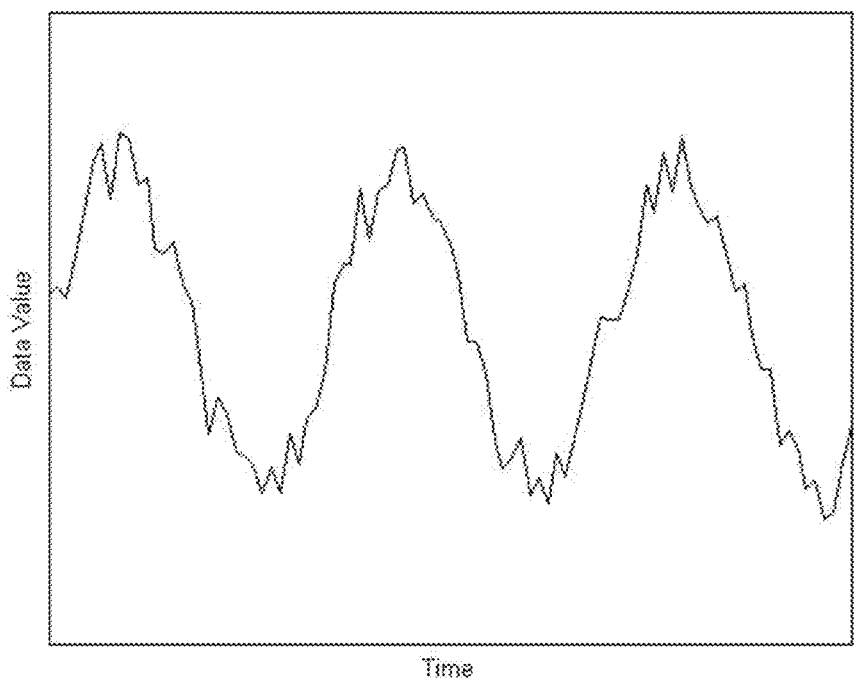
FIG. 5B is a graph indicating the data stream in the graph of FIG. 5A may appear if the user is fatigued.

FIG. 5B demonstrates a data stream as received by the system 100 through the receiver 101 while the user 303 is performing an exercise 302 while fatigued, or while performing with high resistance or performing with high weight 301. The fluctuations in the data stream are caused by muscle quivers. Muscle quivers occur as micro-tears appear in muscles; these tears cause a slackening of the muscle, which is quickly compensated by increased flexion by the muscle. As fatigue sets in, or as resistance is increased, these micro-tears become more common and can compound, causing greater fluctuations in the data set.

The fluctuations in the data between FIG. 5A and FIG. 5B is used by the system 100 in order to estimate the weight 301 that is being used by the user 303 in the exercise 302. The invention depends on data taken at the beginning of an exercise session, or from a previous exercise session, to calculate the fluctuations, and thus estimate the resistance.

In some embodiments, the personal exercise analysis application comprises a software module configured to transmit or receive data associated with 3D bodily motion of a user performing a defined exercise to or from an exercise analysis server application. In further embodiments, the transmission or receiving is direct. In other embodiments, the transmission or receiving is indirect, wherein the data are first transmitted to a digital device. In further embodiments, the digital device is a computer, a mobile device, an online account, an online database, a digital storage medium, a server, a hub, a hard drive, a USB drive, a cloud storage space, or the like.

In some embodiments, the personal exercise analysis application further comprises a software module configured to present an interface allowing a user to create a personal profile. In further embodiments, the profile comprises body weight, height, age, gender, wingspan, fitness expertise, exercise goal, score goal, preference for wearing the device, exercise log, score record, statistical analysis of exercises-related information, or the like.

In some embodiments, the server application comprises a software module configured to apply a probabilistic analysis to data of 3D bodily motion of a user performing a defined exercise to identify an exercise event, classify the exercise type by comparison to one or more of the statistical exercise models, and identify repetitions of the exercise. In further embodiments, the data of 3D bodily motion comprises the acceleration data and the angular velocity data.

In some embodiments, the application comprises a software module configured to apply a statistical analysis to the acceleration data and the angular velocity data to score the user's exercise form. In further embodiments, the score comprises an average score, a personal highest score, a personal lowest score, a score profile over time, a score profile over repetition, or combinations of the like. The comparison method comprises a sum of squared difference, a root mean square deviation, a sum of root mean square deviation, a sum of root mean square, a regression, the Mahalanobis distance, or combinations of the like. In further embodiments, the user's exercise form are scored using a letter grade selecting from a list of A, B, C, D, E, and F. In other embodiments, the user's exercise form is scored using a percentile grade ranging from 100 percentile to 0 percentile. In other embodiments, the user's exercise form is scored using a numerical grade ranging from 10 to 0, 5 to 0, or 4 to 0. In some embodiments, the score is derived, at least in part, from the user's body stability, the user's motion consistency, the user's improvement over time or repetitions, or combinations of the same. In some embodiments, the score is derived, at least in part, from comparison of data of 3D bodily motion of the user to an exercise model generated from a different user or the average of at least two other users' data. In further embodiments, the different user or the other users are one or more qualified fitness professionals, a coach, a personal trainer, an expert, an athlete, a professional player, a robot, or the like.

Figure 8:
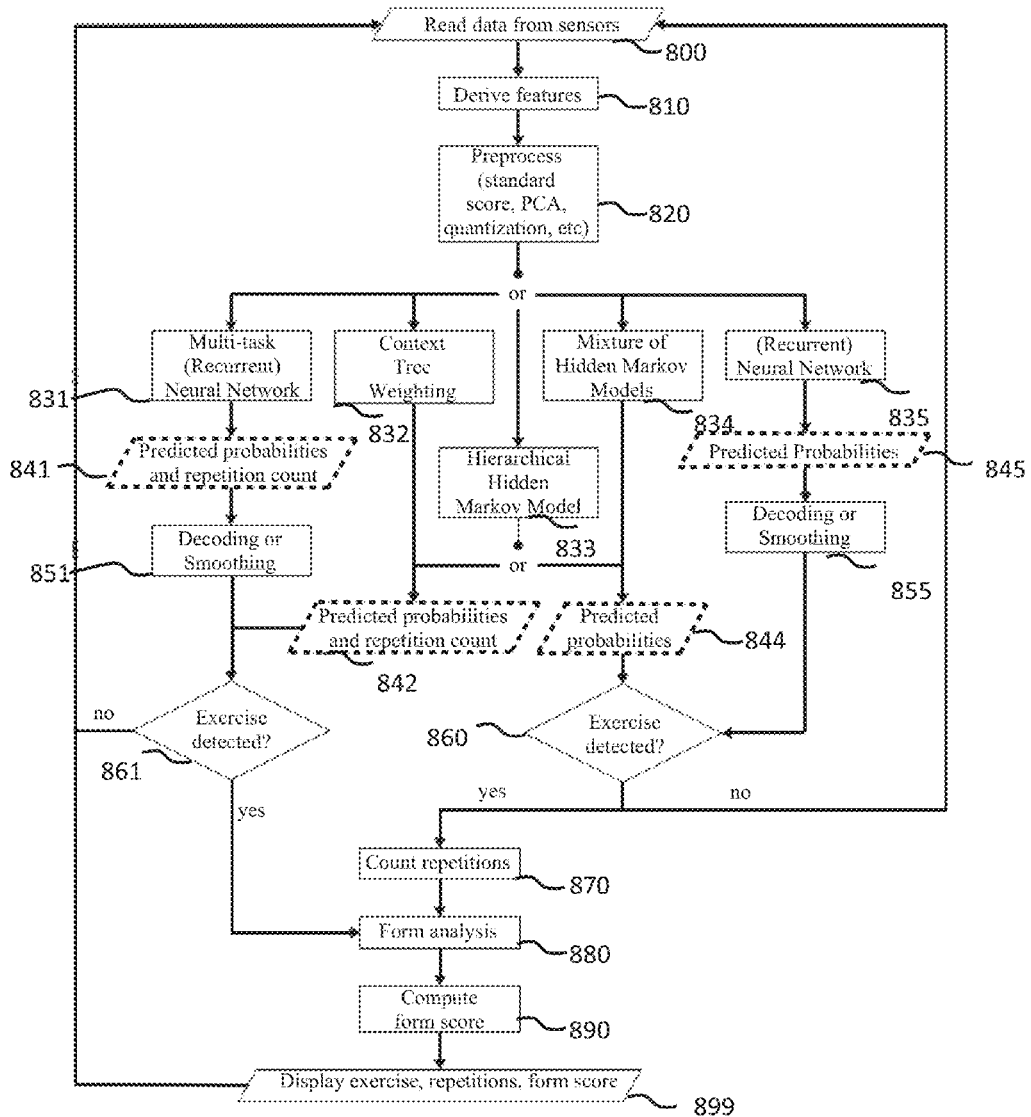
FIG. 8 is a flow chart of analyzing personal bodily motion data using the exemplary embodiment of the personal computing device in FIG. 7.

Referring to FIG. 8, a flow chart of analyzing personal exercise data using the exemplary embodiment of a personal computing device in FIG. 7 is shown. When a user performs a defined exercise with a number of repetitions, the 3D bodily motion data, i.e., the 3D acceleration data and/or the 3D angular velocity data, are read from motion sensors into a personal exercise analysis application 800. Motion sensors optionally include accelerometer and gyroscope. Features of original motion data are derived and optionally selected as inputs 810 to the personal exercise analysis application. Such inputs are optionally preprocessed 820 before feeding into a statistical analysis model 831, 832, 833, 834, or 835. Preprocessing 820 optionally includes computing standard scores or z-scores by subtracting the mean and dividing by standard deviation. Alternatively, PCA (principal component analysis) 820 is performed on the original inputs to remove linear correlation. In this particular embodiment, statistical models are optionally selected from a neural network 831 or 835, a context tree weighting 832, a hidden markov model 833 or 834, or their combinations to estimate the performed exercise and/or the number of repetitions. Also in this embodiment, predicted probabilities associated with the estimated exercise and the estimated number of repetitions 841 or 842 are obtained from the statistical models 831, 832, or 833. In this particular embodiment, the predicted probabilities are a vector of probabilities. An estimated exercise form is generated based on the predicted probabilities associated with the estimated exercise and the estimated number of repetitions 841 or 842. Optionally, the estimated exercise form is further processed to smooth 851 and extract the performed exercise and number of repetitions. When a match between the performed exercise and a recorded exercise is detected 861, the form analysis 880 is performed by comparing the performed exercise data with the recorded exercise, and the form score is calculated based on the comparison 890. Alternatively, only predicted probabilities associated with the estimated exercise 844 or 845 are obtained from the statistical models 833, 834, or 835. An estimated exercise form is generated based on the predicted probabilities associated with the estimated exercise 844 or 845. The estimated exercise form is optionally further processed to smooth 855 and extract the performed exercise and the number of repetitions. When a match between the performed exercise and a recorded exercise is detected 860, the number of repetition is calculated 870, and the form analysis 880 is performed by comparing the performed exercise data with the recorded exercise, and the form score is computed based on the comparison 890. Optionally, the comparison 890 is made via mathematical operations including a root mean square deviation, or a sum of root mean square. Information of the performed exercise type, number of repetitions, and form score are displayed 899 to the user.

Figure 9:
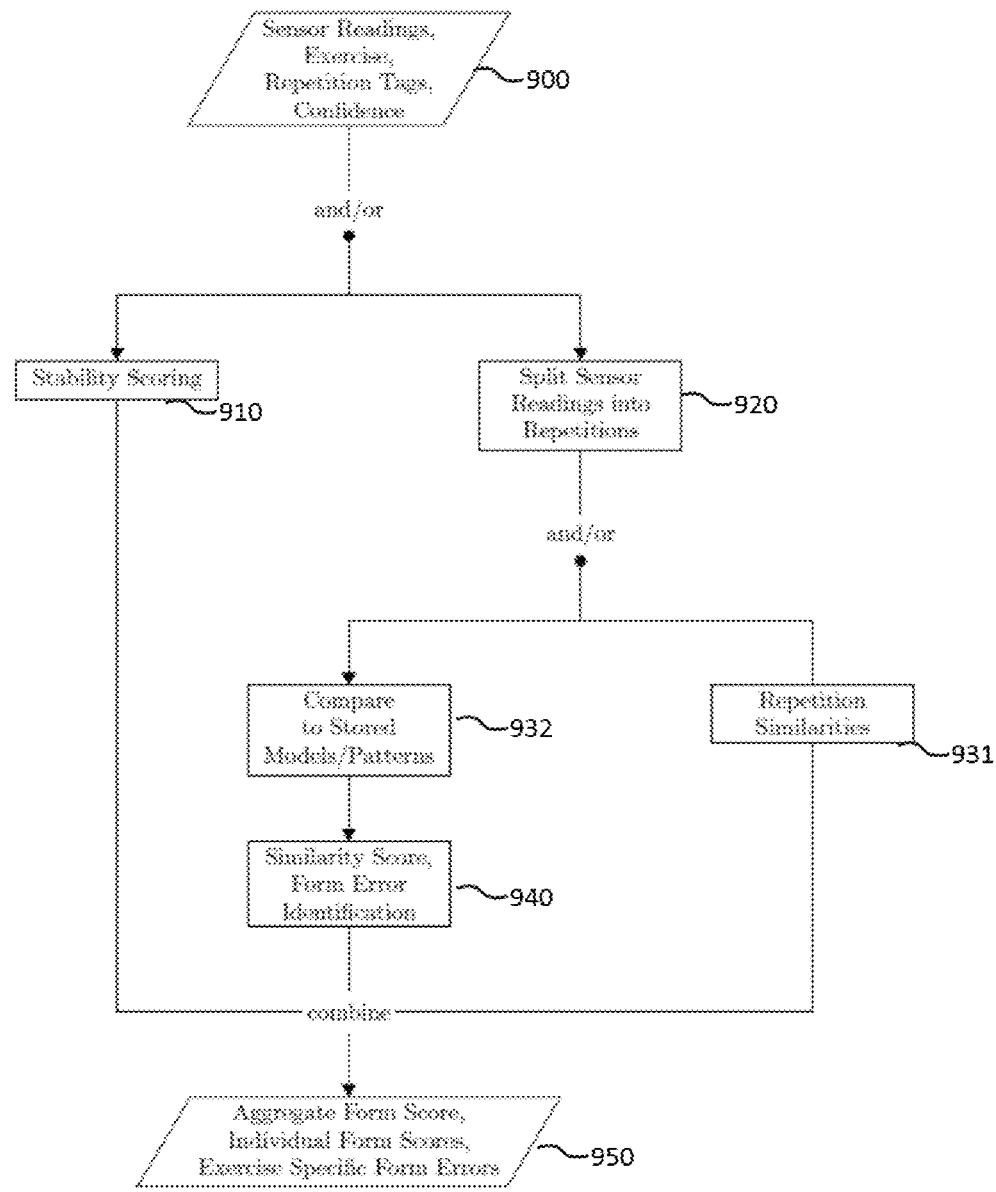
FIG. 9 is a flow chart of scoring a user's exercise form using the exemplary embodiment of the personal computing device in FIG. 7.

FIG. 9 is a flow chart of scoring a user's exercise form using the exemplary embodiment of the personal computing device in FIG. 7. In this particular embodiment, a user performs a defined exercise with repetitions. The 3D bodily motion data obtained from motion sensors 900, for example, accelerometer and gyroscope, associated with the exercise type, number of repetition, and confidence level are used as inputs. The inputs are analyzed for motion stability scoring 910 and/or split into different numbers of repetitions 920. Also in this embodiments, one or more split repetitions are compared to recorded exercise models 932, and a similarity score 940 is generated based on the comparison. Similarities of different numbers of repetitions 931 are optionally evaluated as part of the score, and optionally combined with similarity score 940 and stability score 910 to generate a final score 950. The final score optionally includes aggregated form score and/or individual form score that are displayed to the user. Optionally, in this embodiment, a form error 940 is detected when the similarity score cannot be calculated, and the error message is displayed instead of scores 950.

In some embodiments, the personal exercise analysis application further comprises a software module configured to place the device in a calibration mode, the calibration mode comprising applying a probabilistic analysis to data associated with one or more three-dimensional bodily motions of a specific user to identify user-dependent parameters in the probabilistic models. In some embodiments, the three dimensional bodily motion is raw motion related data collected from the personal computing device. In other embodiments, the 3D bodily motion related data are preprocessed based on raw data collected from motion sensors before the application of a probabilistic analysis. In further embodiments, the preprocessing comprises one or more of space, time, or frequency-related averaging, quantization, denoising, smoothing, linear or non-linear fitting, filtering, weighting, truncating, deleting, transforming, multiplying, subtracting, dividing, interpolating, derivating, rounding, reorganizing, squaring, exponentiation, or the like. In yet further embodiments, the preprocessing comprises mathematical or statistical operation of the raw data including calculating a standard score, a z-score, a quantization, a PCA analysis (principal component analysis), a subtraction of the mean of the raw data, a division by standard deviation of the raw data, or the like.

Exercise Analysis Server Applications

In some embodiments, the devices, platforms, and media described herein include an exercise analysis server application or use of the same. In some embodiments, the server application comprises a database of statistical exercise models. In further embodiments, the database comprises at least 1, at least 2, at least 5, at least 8, at least, 10, at least 20, at least 40, at least 50, at least 80, at least 100, at least 150, at least 250, at least 200, at least 300, at least 400, or at least 500 exercise models, wherein each model is associated with a particular exercise. In further embodiments, a particular exercise model is stored in the database in association with an exercise type, a user gender, a user age, a user weight, a user height, a user wingspan, a number of repetitions, an exercise duration, or combinations of the like. In some embodiments, each exercise model is generated from the average data from a plurality of users performing a defined exercise. In further embodiments, the average data is a weighted average data based on the level of expertise of each user. In some embodiments, one or more exercise models are generated from data from one or more qualified fitness professionals performing a defined exercise. In some embodiments, one or more exercise models is generated from data from a qualified fitness professional performing a defined exercise incorrectly to mimic common exercise form problems. In other embodiments, one or more exercise models are generated from data from a qualified fitness professional performing a defined exercise correctly to illustrate exemplary exercise form. In other embodiments, each exercise model is generated from average data from a single user performing a defined exercise at different numbers of repetitions. In further embodiments, each exercise model is generated from one, two, or three dimensional bodily motion data of a user performing a defined exercise. In further embodiments, the bodily motion data of a user performing the defined exercise are acceleration data received from gyroscope or angular velocity data from accelerometer. In yet further embodiments, the bodily motion data are received from pressure sensor, GPS, timer, or thermometer. In some embodiment, the 3D bodily motion related data of a user comprises one, two, or three dimensional distance, displacement, acceleration, angular velocity, linear momentum, speed, coordinate, geolocation, force, torque, radius, circumference, altitude. In some embodiments, the data received are further related to exercising environment, including atmospheric pressure, water pressure, wind speed, water speed, gravity level, or temperature.

In some embodiments, the exercise analysis server application comprises a software module configured to receive 3D bodily motion related data of a user performing a defined exercise from a personal computing device. In further embodiments, the server application receives receive 3D bodily motion related data of a user performing a defined exercise from at least 5, at least 8, at least 10, at least 20, at least 30, at least 40, at least 50, at least 80, at least 100, at least 200, at least 500, at least 1000, at least 5000, at least 10000, or at least 20000 personal computing devices.

In some embodiments, the server application comprises a software module configured to apply a probabilistic analysis to data of 3D bodily motion of a user performing a defined exercise to identify an exercise event, classify the exercise type by comparison to one or more of the statistical exercise models, and/or identify repetitions of the exercise. In some embodiments, the server application comprises a software module configured to apply a statistical analysis to 3D bodily motion data to score the user's exercise form. In further embodiments, the data of 3D bodily motion comprises the acceleration data and the angular velocity data. In further embodiments, the data of 3D bodily motion comprises one, two, or three dimensional distance, displacement, acceleration, angular velocity, linear momentum, speed, coordinate, geolocation, force, torque, radius, circumference, altitude. In further embodiments, the 3D bodily motion related data of a user comprises mathematical or statistical processing of one, two, or three dimensional distance, displacement, acceleration, angular velocity, linear momentum, speed, coordinate, geolocation, force, torque, radius, circumference, altitude, duration, pressure, or the like. In some embodiments, the data received are further related to exercising environment, including atmospheric pressure, water pressure, wind speed, water speed, gravity level, or temperature.

In some embodiments, the exercise analysis server application further comprises a software module configured to present an interface allowing a user to create, modify, delete or save a personal profile. In further embodiments, the profile comprises body weight, height, age, gender, wingspan, fitness expertise, preference for wearing the device, or the like.

Figure 10:
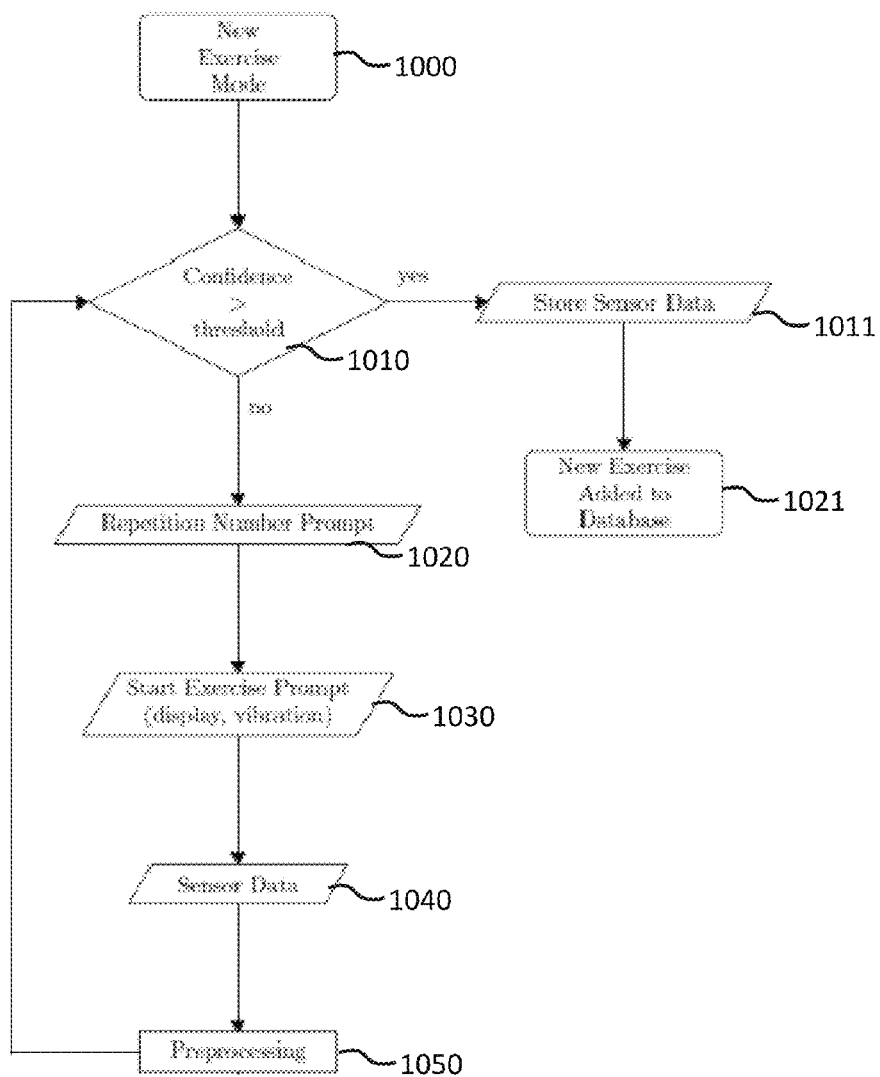
FIG. 10 is a flow chart of recording a new exercise type using the exemplary embodiment of the personal computing device in FIG. 7.

FIG. 10 is a flow chart of recording a new exercise type using the exemplary embodiment of the personal computing device in FIG. 7. In this particular embodiment, a user enters the new exercise mode 1000 and performs a new exercise with a number of repetitions wearing a personal computing device. Motion data are sensed by accelerometer and gyroscope and read to the exercise analysis application. Optionally, when the confidence level of collected data is great than a pre-determined threshold 1010, the motion sensor data are stored and a new exercise is added to the database 1021 in an exercise analysis server application via wireless communication. Also in this embodiment, when the confidence level of motion data is optionally less than a pre-determined threshold 1010, a new number of repetitions are prompted to the user 1020. The user starts to repeat the identical exercise 1030 to generate new motion data 1040. Optionally, the new motion data from the sensor are preprocessed 1050 to reenter the new exercise detection cycle by detecting and comparing a new confidence value to the threshold 1010.

FIG. 1A is a block diagram of an exemplary embodiment of a system 100. An exemplary device can include, for example, a computer having an internal configuration of hardware including a microprocessor 102 and a memory 103. The microprocessor 102 can be a controller for controlling the operations of the portable computing device 100. The microprocessor 102 is connected to the memory 103 by, for example, a memory bus. The memory 103 is optionally FLASH memory, random access memory (RAM), read only memory (ROM) or any other suitable memory device. The memory 103 can store data and program instructions which are used by the microprocessor 102. The program instructions can be in the form of software 104. The software 104 can reside, completely or partially, within the microprocessor 102 or the memory 103. User data receivers 101 can be coupled with the microprocessor 102. Upon reading data from the user data receivers 101, the microprocessor 102 can read the software 104 from the memory 103 to execute analyses on the data. The analyses can be stored in memory 103 or sent to a communication unit 105, wherein a communication unit 105 can send data to another device. The analyses and/or raw data from the user data receivers 101 can be presented to the user with the display 106.

Figure 1B:
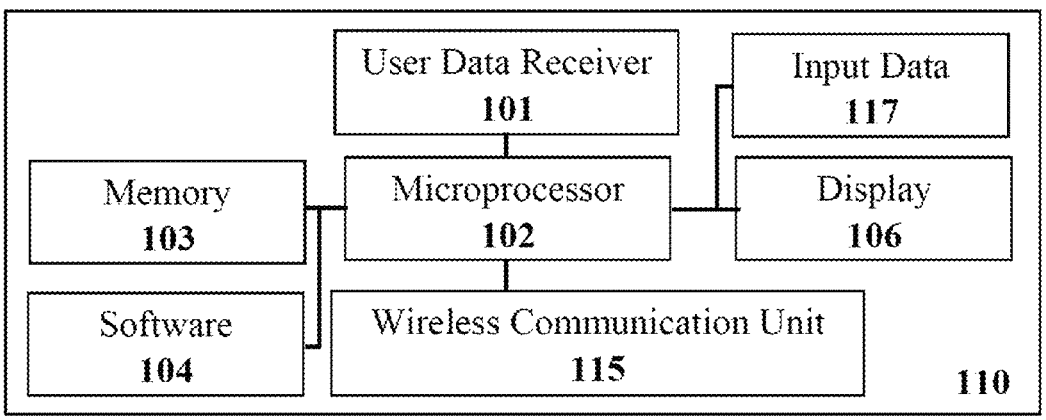
FIG. 1B is a block diagram of one alternative embodiment of a system for integrating wireless communication and user input into a personal data capture device.

FIG. 1B is a block diagram of one embodiment of a system wherein the system 110 is capable of communicating wirelessly 115 and accepting input data 117 from the user.

FIG. 2 is a flow diagram 200 of a method for the analyses of personal data 205 as received by one embodiment of the use 202 of the device 100. Analyses 210 are generated based on the data by the microprocessor 102 of the device with the software 104 on the device. Display feedback 215 is then shown to the user with the display 106. All information in memory 103 can then be transmitted to an auxiliary device 220 with the communication unit 105.

Figure 2B:
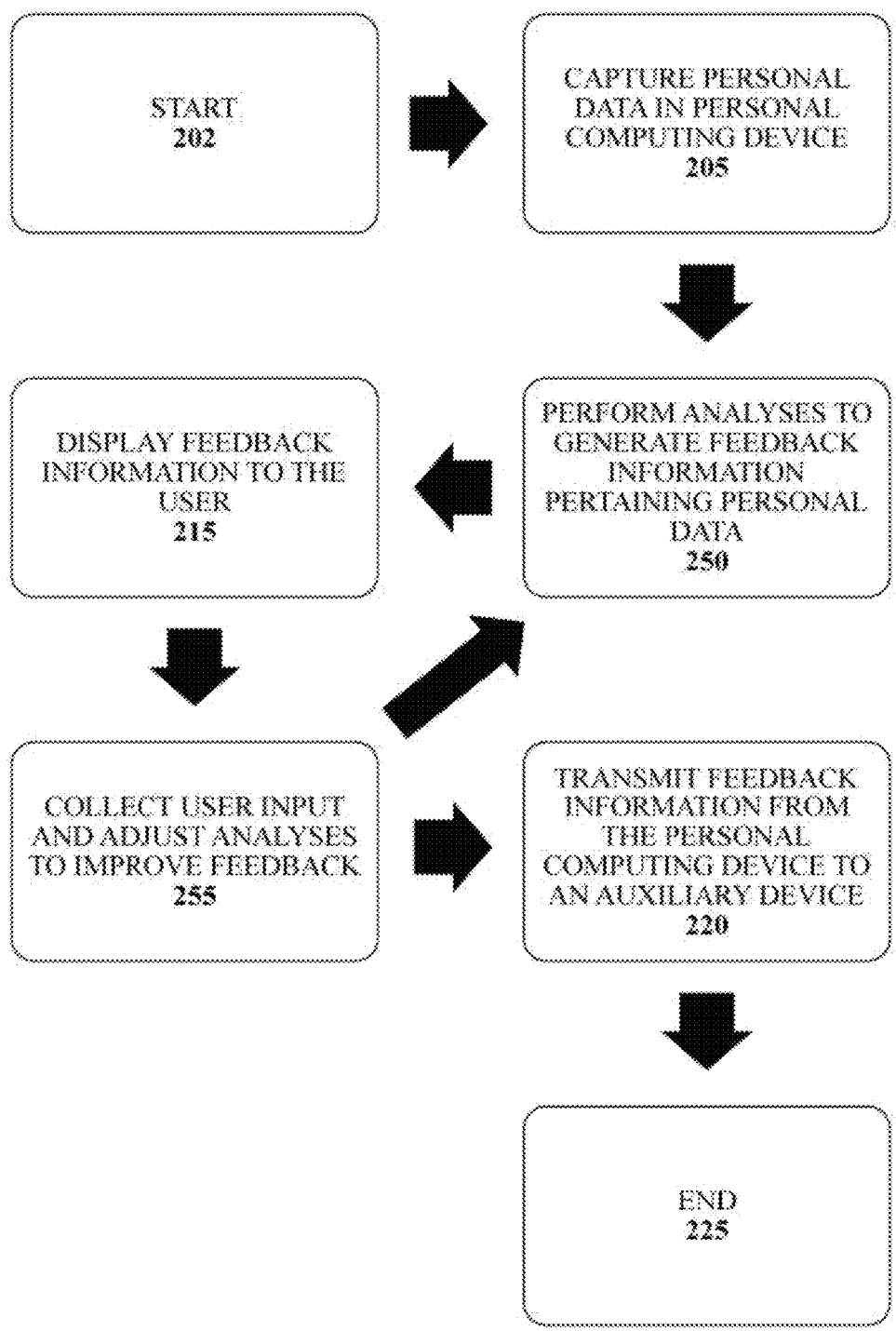
FIG. 2B is a flow diagram of one alternative method for integrating feedback into the analyses of personal data as received by one embodiment of the present invention.

FIG. 2B is a flow diagram 201 of a method for the analyses of personal data 205 as received by one embodiment of the use 202 of the device 110. After display feedback 215 is shown, the device 110 collects user input data 117 and adjusts analyses to improve feedback 255. Further analyses 250 performed by the device 110 can reflect the adjustments based on user input 255.

Exercise Models

In some embodiments, each exercise model is associated with a particular physical exercise. In further embodiments, a particular exercise model is stored in the database in association with an exercise type, a user gender, a user age, a user weight, a user height, a user wingspan, a number of repetitions, an exercise duration, or combinations of the like. In some embodiments, exercise models are added, modified, deleted in the database of the exercise analysis server application or the personal exercise analysis application. In some embodiments, each exercise model is generated from the average data from a plurality of users performing a defined exercise. In further embodiments, the average data is a weighted average data based on the level of expertise of each user. In some embodiments, one or more exercise models are generated from data from one or more qualified fitness professionals performing a defined exercise. In some embodiments, one or more exercise models is generated from data from a qualified fitness professional performing a defined exercise incorrectly to mimic common exercise form problems. In other embodiments, one or more exercise models are generated from data from a qualified fitness professional performing a defined exercise correctly to illustrate exemplary exercise form. In other embodiments, each exercise model is generated from average data from a single user performing a defined exercise at different numbers of repetitions. In further embodiments, each exercise model is generated from one, two, or three dimensional bodily motion data of a user performing a defined exercise. In further embodiments, the bodily motion data of a user performing the defined exercise are acceleration data received from gyroscope or angular velocity data from accelerometer. In yet further embodiments, the bodily motion data are received from pressure sensor, GPS, timer, or thermometer. In some embodiment, the 3D bodily motion related data of a user comprises one, two, or three dimensional distance, displacement, acceleration, angular velocity, linear momentum, speed, coordinate, geolocation, force, torque, radius, circumference, altitude. In some embodiments, the data received are further related to exercising environment, including atmospheric pressure, water pressure, wind speed, water speed, gravity level, or temperature. In some embodiments, one or more exercise models are inputs to the probabilistic analysis in the personal exercise analysis application.

Personal Activity Analysis Applications

In some embodiments, the devices, platforms, and media described herein include a personal activity analysis application or use of the same. In certain embodiments, the personal activity analysis application comprises a software module to receive data associated with a bodily motion of a user in three dimensions. In further embodiments, the data associated with a bodily motion of a user in three dimensions comprise acceleration data and/or angular velocity data. In yet further embodiments, the data associated with a bodily motion of a user in three dimensions are received from one or more selected from accelerometer or gyroscope. In other embodiments, the data associated with a bodily motion of a user in three dimensions are acceleration data. In further embodiments, the data associated with a bodily motion of a user in three dimensions are received from one or more of accelerometers. In some embodiments, acceleration data comprises acceleration information in one, two, or three spatial dimensions and/or one temporal dimension with positive and negative directions for any single dimension, or combinations thereof. In some embodiments, angular velocity data comprises orientation information in one, two, or three spatial dimensions and/or one temporal dimension with positive and negative directions for any single dimension, or combinations thereof. In some embodiments, acceleration data and angular velocity data are three by three vectors. In other embodiments, acceleration data and angular velocity data are four dimensional vectors. In yet further embodiments, the data associated with a bodily motion of a user in three dimensions are received from pressure sensor, GPS, timer, velocity sensor, vibration sensor, or thermometer. In some embodiment, the data associated with a bodily motion of a user in three dimensions comprises one, two, or three dimensional distance, frequency, phase, displacement, acceleration, angular velocity, linear momentum, speed, coordinate, geolocation, force, torque, radius, circumference, altitude, duration, pressure, or the like. In further embodiments, the data associated with a bodily motion of a user in three dimensions comprises mathematical or statistical processing of one, two, or three dimensional distance, displacement, acceleration, angular velocity, linear momentum, speed, coordinate, geolocation, force, torque, radius, circumference, altitude, duration, pressure, or the like. In some embodiments, the data associated with a bodily motion of a user in three dimensions are further related to exercising environment, including atmospheric pressure, water resistance, wind resistance, water pressure, wind speed, water speed, gravity level, or temperature.

In certain embodiments, the personal activity analysis application comprises a software module configured to place the personal computing device in a learning mode. In some embodiments, the learning mode comprises recording of data associated with the bodily motion of a user performing a defined activity in one, two, or three dimensions. In further embodiments, the data associated with the bodily motion of a user in three dimensions are acceleration data and/or angular velocity data of the user performing a defined activity in order to generate a statistical activity model for the activity. In some embodiments, the user is one or more of a qualified fitness professional, a coach, a personal trainer, an expert, an athlete, a professional player, a teacher, an instructor, a lecturer, a robot, or the like. In some embodiments, the activity is a physical activity involving bodily motion in one, two, or three dimensions. In further embodiments, the activities comprises toothbrush, showering, watering, plumbing, trimming, gun shooting, driving, biking, parashooting, cutting, painting, body movement due to gun recoil, typing, sewing, drawing, writing, instrument playing, cleaning, gardening, swimming, hand-shaking, alcohol mixing, bottle opening, video game playing, dancing, or the like. In further embodiments, statistical activity model of a defined activity are generated separately based on activity type, age, body weight, height, gender, wingspan, repetition, or information of the like.

In some embodiments, each activity model is generated from average data from one or more users performing a defined activity. In further embodiments, the average data is a weighted average data based on the level of expertise of each user. In some embodiments, one or more activity models are generated from data from one or more qualified fitness professionals performing a defined activity. In some embodiments, one or more activity models are generated from data from a qualified fitness professional performing a defined activity incorrectly to mimic common activity form problems. In other embodiments, one or more activity models are generated from data from a qualified fitness professional performing a defined activity correctly to illustrate exemplary activity form. In other embodiments, each activity model is generated from average data from a single user performing a defined activity at multiple repetitions. In further embodiments, the statistical models are generated from 3D bodily motion of a user performing a defined activity.

In some embodiments, the personal activity analysis application further comprises a software module configured to place the device in a normal mode, the normal mode comprising applying a probabilistic analysis to data associated with a three-dimensional bodily motion to identify an activity type, classify the activity type by comparison to a recorded activity model, and identify repetitions of the activity. In some embodiments, the three dimensional bodily motion is raw motion related data collected from the personal computing device. In other embodiments, the 3D bodily motion related data are preprocessed based on raw data collected from motion sensors before the application of a probabilistic analysis. In further embodiments, the preprocessing comprises one or more of space, time, or frequency-related averaging, quantization, denoising, smoothing, linear or non-linear fitting, filtering, weighting, truncating, deleting, transforming, multiplying, subtracting, dividing, interpolating, derivation, rounding, reorganizing, squaring, exponentiation, or the like. In yet further embodiments, the preprocessing comprises mathematical or statistical operation of the raw data including calculating a standard score, a z-score, a quantization, a PCA analysis (principal component analysis), a subtraction of the mean of the raw data, a division by standard deviation of the raw data, or the like.

In some embodiments, the probabilistic analysis to classify the activity comprises utilization of a neural network, a context tree weighting, a hidden markov model, a dynamic system, a principal component analysis, a k-mean clustering, a dynamic Bayesian network, a mixture model, a regression model, a markov random field, a conditional random field, a template matching, a dynamic probabilistic graphical model, a K-nearest neighbors model, a patent recognition model, a statistical learning model, a machine learning model, or combinations of the same. In some embodiments, the inputs to the probabilistic analysis include the unprocessed bodily motion data in one, two, or three dimensions of a user performing one or more defined activities. In further embodiments, the inputs to the probabilistic analysis include the preprocessed bodily motion data in one, two, or three dimensions of a user performing one or more defined activities. In further embodiments, the preprocessing is by mathematical or statistical operations. In some embodiments, the inputs to the probabilistic analysis comprise one or more recorded activity models. In some embodiments, the outputs of the probabilistic analysis comprise probabilities, vector of probabilities, significance, vector of significance, p values, vector of p values, estimation error, vector of estimation errors, or the like. In further embodiments, the output values are greater than or equal to 0 and less or equal to 1. In further embodiments, the outputs of the probabilistic analysis have a fixed sum. In yet further embodiments, the outputs of the probabilistic analysis have a sum of 1.

In some embodiments, the personal activity analysis application further comprises a software module configured to apply a comparison method to data of 3D bodily motion to score the user's activity form. In further embodiments, the score comprises an average score, a personal highest score, a personal lowest score, a score profile over time, a score profile over repetition, or combinations of the like. The comparison method comprises a sum of squared difference, a statistical divergence, a root mean square deviation, a sum of root mean square deviation, a sum of root mean square, a regression, the Mahalanobis distance, or combinations of the like. In further embodiments, the user's activity form are scored using a letter grade selecting from a list of A, B, C, D, E, and F. In other embodiments, the user's activity form is scored using a percentile grade ranging from 100 percentile to 0 percentile. In other embodiments, the user's activity form is scored using a numerical grade ranging from 10 to 0, 5 to 0, or 4 to 0. In some embodiments, the score is derived, at least in part, from the user's body stability, the user's motion consistency, the user's improvement over time or repetitions, or combinations of the same. In some embodiments, the score is derived, at least in part, from comparison of data of 3D bodily motion of the user to an activity model generated from a different user or the average of at least two other users' data. In further embodiments, the different user or the other users are one or more qualified fitness professionals, a coach, a personal trainer, an expert, an athlete, a professional player, a robot, or the like.

In some embodiments, the application further comprises a software module configured to present a user interface, the user interface allow user-device interaction via an input device. In further embodiments, the input device comprises a touchscreen, a key, a button, a scroll, a mouse, a keyboard, a pointing device, a remote control, a microphone, a motion sensor, an eye movement sensor, a temperature sensor, an optical sensor, or a pressure sensor. In further embodiments, the interaction comprises a touch, a click, a vibration, a shake, a tap, highlighting, circling, contouring, a gesture, pointing, swiping, pressing, an eye movement, or crossing. In some embodiments, the user interface allow an on-device display of message, a selection or a modification of a device mode, a rest timer, an instantaneous feedback via sound, light, or vibration, a device calibration, a report of error, a correction of error, an activity-related reminder, a physiological data-related reminder, or a combination thereof. In further embodiments, the instantaneous feedback comprises feedback of the physiological data of the user or the activity-related performance of the user via sound, light, or vibration. In some embodiments, the on-device display comprises display of a score, an activity type, a number of repetitions, level of muscle fatigue, activity duration, an activity-specific message, physiological data of the user, a device-related message, a storage space usage, a battery level, a number of stored activity related, an exercise log, a user profile, or the like. In further embodiments, the graphic user interface allows a user to make a correction to activity-related information, and/or activity-related information with one or more mathematical or statistical operations. In further embodiments, the activity-related information includes an activity type, a number of repetitions, an activity log, a score, an average score, an average duration, an average weight, a total duration, a total score, a minimal or maximal score, a score log, a weight, a duration, or any activity-derived information. In further embodiments, a correction to activity related information is used to update statistical analysis or probabilistic analysis methods.

In some embodiments, the activity is a weight training activity, and the activity-specific message comprises: time spent, number of repetitions, weight too much, weight too litter, weight changed too much, motion too fast, body too unstable, form too incorrect, form too inconsistent, number of activity stored, and corrective advice regarding activity form. In some embodiments, the device-specific message comprises: Bluetooth connected, Bluetooth disconnected, total number of activities stored, new activity type added, activity type deleted, activity type error, low storage space, battery level notification, geolocation detected, reset timer started, reset timer stopped, geolocation error, environment detected, environment error, or combinations of the like.

In some embodiments, the personal activity analysis application comprises a software module configured to transmit or receive data associated with 3D bodily motion of a user performing a defined activity to or from an activity analysis server application. In further embodiments, the transmission or receiving is direct. In other embodiments, the transmission or receiving is indirect, wherein the data are first transmitted to a digital device. In further embodiments, the digital device is a computer, a mobile device, an online account, an online database, a digital storage medium, a server, a hub, a hard drive, a USB drive, a cloud storage space, or the like.

In some embodiments, the personal activity analysis application further comprises a software module configured to present an interface allowing a user to create a personal profile. In further embodiments, the profile comprises body weight, height, age, gender, wingspan, fitness expertise, activity goal, score goal, preference for wearing the device, activity log, score record, statistical analysis of activities-related information, or the like.

In some embodiments, the server application comprises a software module configured to apply a probabilistic analysis to data of 3D bodily motion of a user performing a defined activity to identify an activity event, classify the activity type by comparison to one or more of the statistical activity models, and identify repetitions of the activity. In further embodiments, the data of 3D bodily motion comprises the acceleration data and the angular velocity data.

In some embodiments, the application comprises a software module configured to apply a statistical analysis to the acceleration data and the angular velocity data to score the user's activity form. In further embodiments, the score comprises an average score, a personal highest score, a personal lowest score, a score profile over time, a score profile over repetition, or combinations of the like. The comparison method comprises a sum of squared difference, a root mean square deviation, a sum of root mean square deviation, a sum of root mean square, a regression, the Mahalanobis distance, or combinations of the like. In further embodiments, the user's activity form are scored using a letter grade selecting from a list of A, B, C, D, E, and F. In other embodiments, the user's activity form is scored using a percentile grade ranging from 100 percentile to 0 percentile. In other embodiments, the user's activity form is scored using a numerical grade ranging from 10 to 0, 5 to 0, or 4 to 0. In some embodiments, the score is derived, at least in part, from the user's body stability, the user's motion consistency, the user's improvement over time or repetitions, or combinations of the same. In some embodiments, the score is derived, at least in part, from comparison of data of 3D bodily motion of the user to an activity model generated from a different user or the average of at least two other users' data. In further embodiments, the different user or the other users are one or more qualified fitness professionals, a coach, a personal trainer, an expert, an athlete, a professional player, a robot, or the like.

In some embodiments, the personal activity analysis application further comprises a software module configured to place the device in a calibration mode, the calibration mode comprising applying a probabilistic analysis to data associated with one or more three-dimensional bodily motions of a specific user to identify user-dependent parameters in the probabilistic analysis. In some embodiments, the three dimensional bodily motion is raw motion related data collected from the personal computing device. In other embodiments, the 3D bodily motion related data are preprocessed based on raw data collected from motion sensors before the application of a probabilistic analysis. In further embodiments, the preprocessing comprises one or more of space, time, or frequency-related averaging, quantization, denoising, smoothing, linear or non-linear fitting, filtering, weighting, truncating, deleting, transforming, multiplying, subtracting, dividing, interpolating, derivating, rounding, reorganizing, squaring, exponentiation, or the like. In yet further embodiments, the preprocessing comprises mathematical or statistical operation of the raw data including calculating a standard score, a z-score, a quantization, a PCA analysis (principal component analysis), a subtraction of the mean of the raw data, a division by standard deviation of the raw data, or the like.

Activity Analysis Server Applications

In some embodiments, the devices, platforms, and media described herein include an activity analysis server application or use of the same. In some embodiments, the server application comprises a database of statistical activity models. In further embodiments, the database comprises at least 1, at least 2, at least 5, at least 8, at least, 10, at least 20, at least 40, at least 50, at least 80, at least 100, at least 150, at least 250, at least 200, at least 300, at least 400, or at least 500 activity models, wherein each model is associated with a particular activity. In further embodiments, a particular activity model is stored in the database in association with an activity type, a user gender, a user age, a user weight, a user height, a user wingspan, a number of repetitions, an activity duration, or combinations of the like. In some embodiments, each activity model is generated from the average data from a plurality of users performing a defined activity. In further embodiments, the average data is a weighted average data based on the level of expertise of each user. In some embodiments, one or more activity models are generated from data from one or more qualified fitness professionals performing a defined activity. In some embodiments, one or more activity models are generated from data from a qualified fitness professional performing a defined activity incorrectly to mimic common activity form problems. In other embodiments, one or more activity models are generated from data from a qualified fitness professional performing a defined activity correctly to illustrate exemplary activity form. In other embodiments, each activity model is generated from average data from a single user performing a defined activity at different numbers of repetitions. In further embodiments, each activity model is generated from one, two, or three dimensional bodily motion data of a user performing a defined activity. In further embodiments, the bodily motion data of a user performing the defined activity are acceleration data received from gyroscope or angular velocity data from accelerometer. In yet further embodiments, the bodily motion data are received from pressure sensor, GPS, timer, or thermometer. In some embodiment, the 3D bodily motion related data of a user comprises one, two, or three dimensional distance, displacement, acceleration, angular velocity, linear momentum, speed, coordinate, geolocation, force, torque, radius, circumference, altitude. In some embodiments, the data received are further related to exercising environment, including atmospheric pressure, water pressure, wind speed, water speed, gravity level, or temperature.

In some embodiments, the activity analysis server application comprises a software module configured to receive 3D bodily motion related data of a user performing a defined activity from a personal computing device. In further embodiments, the server application receives receive 3D bodily motion related data of a user performing a defined activity from at least 5, at least 8, at least 10, at least 20, at least 30, at least 40, at least 50, at least 80, at least 100, at least 200, at least 500, at least 1000, at least 5000, at least 10000, or at least 20000 personal computing devices.

In some embodiments, the server application comprises a software module configured to apply a probabilistic analysis to data of 3D bodily motion of a user performing a defined activity to identify an activity event, classify the activity type by comparison to one or more of the statistical activity models, and/or identify repetitions of the activity. In some embodiments, the server application comprises a software module configured to apply a statistical analysis to 3D bodily motion data to score the user's activity form. In further embodiments, the data of 3D bodily motion comprises the acceleration data and the angular velocity data. In further embodiments, the data of 3D bodily motion comprises one, two, or three dimensional distance, displacement, acceleration, angular velocity, linear momentum, speed, coordinate, geolocation, force, torque, radius, circumference, altitude. In further embodiments, the 3D bodily motion related data of a user comprises mathematical or statistical processing of one, two, or three dimensional distance, displacement, acceleration, angular velocity, linear momentum, speed, coordinate, geolocation, force, torque, radius, circumference, altitude, duration, pressure, or the like. In some embodiments, the data received are further related to exercising environment, including atmospheric pressure, water pressure, wind speed, water speed, gravity level, or temperature.

In some embodiments, the activity analysis server application further comprises a software module configured to present an interface allowing a user to create, modify, delete or save a personal profile. In further embodiments, the profile comprises body weight, height, age, gender, wingspan, fitness expertise, preference for wearing the device, or the like.

Activity Models

In some embodiments, each activity model is associated with a particular physical activity. In further embodiments, a particular activity model is stored in the database in association with an activity type, a user gender, a user age, a user weight, a user height, a user wingspan, a number of repetitions, an activity duration, or combinations of the like. In some embodiments, activity models are added, modified, deleted in the database of the activity analysis server application or the personal activity analysis application. In some embodiments, each activity model is generated from the average data from a plurality of users performing a defined activity. In further embodiments, the average data is a weighted average data based on the level of expertise of each user. In some embodiments, one or more activity models are generated from data from one or more qualified fitness professionals performing a defined activity. In some embodiments, one or more activity models are generated from data from a qualified fitness professional performing a defined activity incorrectly to mimic common activity form problems. In other embodiments, one or more activity models are generated from data from a qualified fitness professional performing a defined activity correctly to illustrate exemplary activity form. In other embodiments, each activity model is generated from average data from a single user performing a defined activity at different numbers of repetitions. In further embodiments, each activity model is generated from one, two, or three dimensional bodily motion data of a user performing a defined activity. In further embodiments, the bodily motion data of a user performing the defined activity are acceleration data received from gyroscope or angular velocity data from accelerometer. In yet further embodiments, the bodily motion data are received from pressure sensor, GPS, timer, or thermometer. In some embodiment, the 3D bodily motion related data of a user comprises one, two, or three dimensional distance, displacement, acceleration, angular velocity, linear momentum, speed, coordinate, geolocation, force, torque, radius, circumference, altitude. In some embodiments, the data received are further related to exercising environment, including atmospheric pressure, water pressure, wind speed, water speed, gravity level, or temperature. In some embodiments, one or more activity models are inputs to the probabilistic analysis in the personal activity analysis application.

Digital Processing Device

In some embodiments, the platforms, media, methods and applications described herein include a digital processing device, a processor, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In some embodiments, the non-volatile memory comprises the Magnetoresistive random-access memory (MRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In some embodiments, the display is E-paper or E ink. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Non-Transitory Computer Readable Storage Medium

In some embodiments, the platforms, media, methods and applications described herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, media, methods and applications described herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows®

Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

In some embodiments, the platforms, media, methods and applications described herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of barcode, route, parcel, user, or network information. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Web Browser Plug-in

In some embodiments, the computer program includes a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, sub-notebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

EXAMPLES

The following illustrative examples are representative of embodiments of the applications, systems, methods, and media described herein and are not meant to be limiting in any way.

Example 1

Learning a New Exercise

A weightlifting coach wears the personal computing devices on his right wrist. He enters his body weight, height, age and gender as the information that will be stored with the exercises he selects to perform. He also enters the weight and number of dumbbell that he selects to use. After he properly enters the new exercise identification model, and started recording, he performs flat chest dumbbell raise using both hands with two dumbbells of 10 pounds each. He repeated the same exercise for 3 groups with 10 repetitions in each group. To minimize muscle fatigue, each group is finished in 1 minute and separated by a 2 minute gap in between. After he finishes the whole set of exercises, he use the user interface on the personal computing device to save the new exercise. The confidence level is greater than the preset threshold, and the motion data was saved and added to the database of exercises in association with exercise type, body weight, height, age, gender, and the dumbbell number and weight.

Example 2

Working Out a Recorded Exercise

A graduate student wears the personal computing device on his right wrist and selects his user profile that has been saved in the personal computing device via the graphic user interface. He enters the working out mode after his user profile has been selected and confirmed. The graduate student performs flat chest dumbbell raise using both hands with two dumbbells of 3 pounds each. He repeated the same exercise for 1 group with 10 repetitions. His exercising data is compared to the recorded exercise types, an exercise score is not calculated and a message is displayed as "weight too light" on the device. He switches to one dumbbell of 10 pounds and repeats flat chest dumbbell raise using his right arm. He repeats the exercise for another 10 repetitions, and prompts the device to calculate a score again. A message of "body too unstable" is displayed with an exercise form score of 50%. The graduate student decided to try it again and choose to repeat the flat dumbbell raise using both hands and 10 pound dumbbells. He repeats the exercises for 10 times carefully thus slowly in 2.5 minutes. The exercise form score shows a 70% on display with a message "motion too slow or weight too much." In his third attempt to perform the exercise, he turned on the instantaneous vibration feedback using the graphic user interface. When he performs the exercise for the first three repetitions, one vibration is given as an indication of keeping a good form, as he reaches the 15's repetition; two continuous vibrations are given as an indication of inaccurate form due to muscle fatigue. The total form score of his third attempt is 85% based on the total of 20 repetitions.

What is claimed is:

1. A personal computing device comprising:
   a. a processor, an onboard memory, an accelerometer, a gyroscope, and a display;
   b. a computer program including instructions executable by the personal computing device to create an exercise analysis application comprising:
      i. a software module configured to receive acceleration data from the accelerometer and angular velocity data from the gyroscope, the acceleration data and the angular velocity data associated with the bodily motion of a user in three dimensions;
      ii. a software module configured to place the device in a learning mode, the learning mode comprising recording the acceleration data, the angular velocity data, and repetitions of the user performing a defined exercise to generate a statistical exercise model for the exercise;
      iii. a software module configured to place the device in a normal mode, the normal mode comprising applying a probabilistic analysis to the acceleration data and the angular velocity data to identify an exercise event, classify the exercise by comparison to a recorded exercise model, and simultaneously identify repetitions of the exercise; and
      iv. a software module configured to apply a statistical analysis to the acceleration data and the angular velocity data to score the user's exercise form.

2. The device of claim 1, wherein the device is adapted to be user-wearable.

3. The device of claim 2, wherein the device is adapted to be wrist-wearable by the user.

4. The device of claim 2, wherein the device comprises a wearable adapter, the wearable adapter reversibly connectable from the device to form a modular design.

5. The device of claim 1, further comprising a biosensor to measure a physiological parameter of the user.

6. The device of claim 5, wherein the biosensor is selected from the group consisting of: a heart rate monitor, a thermometer, a respirometer, a glucose monitor, an electrolyte sensor, and an electrical conductance meter.

7. The device of claim 5, wherein the biosensor is an optical biosensor.

8. The device of claim 5, wherein the physiological parameter is selected from the group consisting of: heart rate, skin temperature, breathing rate, galvanic skin response, and hydration.

9. The device of claim 5, wherein the application further comprises a software module configured to present a graphic user interface comprising a heart rate-based rest timer.

10. The device of claim 1, further comprising a geolocation element.

11. The device of claim 1, further comprising a wireless communications element.

12. The device of claim 11, wherein the wireless communications element is a Bluetooth module or an ANT+ module.

13. The device of claim 1, wherein the probabilistic analysis to classify the exercise comprises utilization of a neural network, context tree weighting, hidden markov models, or a combination thereof.

14. The device of claim 1, wherein the score is derived, at least in part, from the user's body stability, the user's motion consistency, or a combination thereof.

15. The device of claim 1, wherein the score is derived, at least in part, from comparison of the acceleration data and the angular velocity data to an exercise model generated from other users' data.

16. The device of claim 1, wherein the score is derived, at least in part, from comparison of the acceleration data and the angular velocity data to an exercise model generated from one or more qualified fitness professionals.

17. The device of claim 1, wherein the exercise is a unilateral weight training exercise or a bilateral weight training exercise.

18. The device of claim 1, wherein the application further comprises a software module configured to present a user interface on the display, the user interface comprising the score, the exercise, the repetitions, exercise-specific messages, or a combination thereof.

19. The device of claim 18, wherein the exercise is a weight training exercise and the exercise-specific messages are suggestions selected from the group consisting of: weight too heavy, weight too light, weight changed too much, motion too fast, body too unstable, form incorrect, form too inconsistent, and corrective advice regarding form.

20. An exercise analysis platform comprising:
   a. a personal computing device comprising a processor, an onboard memory, an accelerometer, a gyroscope, a display, and a communications element, the device configured to provide an personal exercise analysis application comprising:
   i. a software module configured to receive acceleration data from the accelerometer and angular velocity data from the gyroscope, the acceleration data and the angular velocity data associated with the bodily motion of a user in three dimensions;
   ii. a software module configured to transmit the acceleration data and angular velocity data to an exercise analysis server application;
  b. a server processor configured to provide the exercise analysis server application comprising:
   i. a database of statistical exercise models, the exercise models generated from acceleration data, angular velocity data, and repetitions of the user performing a defined exercise;
   ii. a software module configured to receive acceleration data and angular velocity data from the personal computing device;
   iii. a software module configured to apply a probabilistic analysis to the acceleration data and the angular velocity data to identify an exercise event, classify the exercise by comparison to one or more of the statistical exercise models, and simultaneously identify repetitions of the exercise;
   iv. a software module configured to apply a statistical analysis to the acceleration data and the angular velocity data to score the user's exercise form.

21. The platform of claim 20, comprising at least 100, at least 1000, or at least 10,000 personal computing devices.

22. The platform of claim 20, wherein the personal exercise analysis application further comprises a software module configured to place the personal computing device in a learning mode, the learning mode comprising recording the acceleration data and the angular velocity data of the user performing a defined exercise to generate a statistical exercise model for the exercise.

23. The platform of claim 20, wherein the database of statistical exercise models comprises at least 10, at least 50, at least 100, or at least 500 exercise models, each exercise model associated with a particular exercise.

24. The platform of claim 20, wherein each exercise model is generated from averaged data from a plurality of users performing a defined exercise.

25. The platform of claim 20, wherein one or more exercise models are generated from data from one or more qualified fitness professionals performing a defined exercise.

26. The platform of claim 25, wherein one or more exercise models are generated from data from a qualified fitness professional performing a defined exercise incorrectly to mimic common exercise form problems.

27. The platform of claim 25, wherein one or more exercise models are generated from data from a qualified fitness professional performing a defined exercise correctly to illustrate exemplary exercise form.

28. The platform of claim 20, wherein the personal exercise analysis application or the server application further comprises a software module configured to present an interface allowing the user to create a personal profile, the profile comprising weight, height, gender, wingspan, and fitness expertise.

29. Non-transitory computer-readable storage media encoded with instructions executable by a processor to perform personal exercise analysis, the instructions comprising:
  a. a software module configured to receive data from a personal computing device comprising an accelerometer and a gyroscope, the data comprising acceleration data from the accelerometer and angular velocity data from the gyroscope, the acceleration data and the angular velocity data associated with the bodily motion of a user in three dimensions;
  b. a software module configured to place the device in a learning mode, the learning mode comprising recording the acceleration data, angular velocity data, and repetitions of the user performing a defined exercise to generate a statistical exercise model for the exercise;
  c. a software module configured to place the device in a normal mode, the normal mode comprising applying a probabilistic analysis to the acceleration data and the angular velocity data to identify an exercise event, classify the exercise by comparison to a recorded exercise model, and simultaneously identify repetitions of the exercise; and
  d. a software module configured to apply a statistical analysis to the acceleration data and the angular velocity data to score the user's exercise form.

30. Non-transitory computer-readable storage media encoded with a computer program including instructions executable by a processor to create an exercise analysis server application comprising:
  a. a database of statistical exercise models, the exercise models generated from acceleration data, angular velocity data, and repetitions transmitted by a personal computing device associated with a user performing a defined exercise, the acceleration data and the angular velocity data each comprising data for X, Y, and Z-axes, the device in a learning mode;
  b. a software module configured to receive acceleration data and angular velocity data transmitted by the personal computing device associated with a user performing a defined exercise, the device in a normal mode;
  c. a software module configured to apply a probabilistic analysis to the received acceleration data and angular velocity data to identify an exercise event, classify the exercise by comparison to one or more of the statistical exercise models, and simultaneously identify repetitions of the exercise;
  d. a software module configured to apply a statistical analysis to the received acceleration data and angular velocity data to score the user's exercise form.

* * * * *